United States Patent [19]
Suarato et al.

[11] Patent Number: 6,096,888
[45] Date of Patent: Aug. 1, 2000

[54] ANTHRACYCLINONE DERIVATIVES AND THEIR USE IN AMYLOIDOSIS

[75] Inventors: Antonino Suarato, Milan; Jacqueline Lansen, San Vittore Olona; Michele Caruso, Milan; Dario Ballinari, San Donato Milanese; Tiziano Bandiera, Gambolo, all of Italy

[73] Assignee: Pharmacia & Upjohn S.p.A., Milan, Italy

[21] Appl. No.: 09/395,202

[22] Filed: Sep. 14, 1999

Related U.S. Application Data

[62] Division of application No. 08/946,578, Oct. 7, 1997, Pat. No. 5,998,615, which is a division of application No. 08/615,182, Apr. 4, 1996, Pat. No. 5,731,313, and a continuation of application No. PCT/EP95/02928, Jul. 24, 1995.

[30] Foreign Application Priority Data

Aug. 8, 1994 [GB] United Kingdom .................... 9416007

[51] Int. Cl.⁷ ................................................ C07D 295/108
[52] U.S. Cl. .......................... 544/154; 544/380; 546/195; 546/285; 548/528
[58] Field of Search .................................... 544/154, 380; 546/195; 548/528

[56] References Cited

U.S. PATENT DOCUMENTS 5,744,454   4/1998   Suarato et al. ............................ 536/6.4

OTHER PUBLICATIONS

Hartmann et al, Chemical Abstracts, vol. 126, No. 144,048 (1997).

Sumitomo, Chemical Abstracts, vol. 103, No. 141,751 (1985).

Povarov et al. Chemical Abstracts, vol. 91, No. 20926 (1979).

*Primary Examiner*—Robert W. Ramsuer
*Attorney, Agent, or Firm*—Oblon, Spivak, McClelland, Maier & Neustadt, P.C.

[57] ABSTRACT

The present invention provides the new use in the treatment of amyloidosis with the anthracyclinone of formula (A) wherein R1, R2, R3, R4, and R5, are appropriate substituents. Some compounds of formula (A) are novel. Processes for their preparation and pharmaceutical composition containing them are also described.

6 Claims, No Drawings

ANTHRACYCLINONE DERIVATIVES AND THEIR USE IN AMYLOIDOSIS

This application is a Division of applicaton Ser. No. 08/946,578, filed on Oct. 7,1997, now U.S. Pat. No. 5,998, 615 which is a Division of application Ser. No. 08/615,182, filed on Apr. 4, 1996 (now U.S. Pat. No. 5,731,313), which was originally filed as International Application No. PCT/EP95/02928, filed Jul. 24, 1995.

The present invention relates to treating amyloidosis, to novel compounds for such treatment, to processes for their preparation and to pharmaceutical compositions containing them.

The relationship between amyloidosis, cell death and loss of tissue function appears to be of relevance for different types of disorders including neurodegenerative disorders. Therefore, the prevention of amyloid formation and/or the induction of amyloid degradation can be an important therapeutic tool for all pathological disorders associated with amyloidosis including AL amyloidosis and neurodegenerative disorders of the Alzheimer's type.

More particularly, the present invention provides the use in the manufacture of a medicament for use in the treatment of amyloidosis of an anthracyclinone of formula A

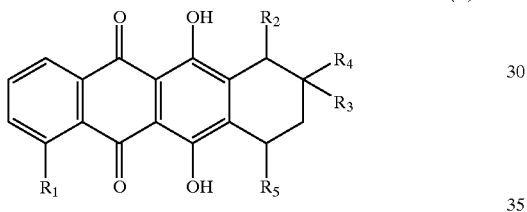

(A)

wherein $R_1$ represents:
  hydrogen or hydroxy;
  a group of formula $OR_6$ in which $R_6$ is $C_1$–$C_6$ alkyl, $C_{5-6}$ cycloalkyl or $CH_2Ph$ with the phenyl (Ph) ring optionally substituted by 1, 2 or 3 substituents selected from F, Cl, Br, $C_1$–$C_6$ alkyl, $C_1$–$C_6$ alkoxy and $CF_3$; or
  a group of formula $OSO_2R_7$ in which $R_7$ is $C_1$–$C_6$ alkyl or Ph optionally substituted by 1, 2 or 3 substituents selected from halogen, such as F, Cl or Br, and $C_1$–$C_6$ alkyl;

$R_2$ represents hydrogen, hydroxy, $OR_6$, COOH or $COOR_6$ wherein
$R_6$ is as above defined;

$R_3$ represents hydrogen, hydroxy or $OR_6$ as above defined;

$R_4$ represents hydrogen, methyl or a group of formula $XCH_2R_8$ in which X is CO, $CH_2$, CHOH or a group of formula

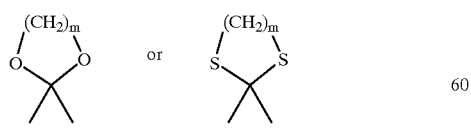

in which m is 2 or 3 and $R_8$ is:
  hydrogen or hydroxy;
  a group of formula $NR_9R_{10}$ in which:
    $R_9$ and $R_{10}$ are each independently selected from:

(a) hydrogen,
(b) a $C_1$–$C_6$ alkyl or $C_2$–$C_6$ alkenyl group optionally substituted with hydroxy, CN, $COR_{11}$, $COOR_{11}$, $CONR_{11}R_{12}$, $O(CH_2)_nNR_{11}R_{12}$ (n is 2 to 4) or $NR_{11}R_{12}$ in which $R_{11}$ and $R_{12}$ are each independently selected from hydrogen, a $C_1$–$C_{12}$ alkyl or $C_2$–$C_{12}$ alkenyl group or phenyl optionally substituted by one or more, for example 1, 2 or 3, substituents selected from $C_1$–$C_6$ alkyl, $C_1$–$C_6$ alkoxy, F, Br, Cl, $CF_3$, OH, $NH_2$ or CN,
(c) $C_{3-6}$ cycloalkyl optionally substituted with $COR_{11}$, $COOR_{11}$ or OH wherein $R_{11}$ is as above defined,
(d) phenyl($C_1$–$C_4$ alkyl or $C_2$–$C_4$ alkenyl) optionally substituted on the phenyl ring by one or more, for example 1, 2 or 3, substituents selected from $C_1$–$C_6$ alkyl, $C_1$–$C_6$ alkoxy, F, Br, Cl, $CF_3$, OH, $NH_2$ or CN, or
(e) $COR_{11}$, $COOR_{11}$, $CONR_{11}R_{12}$, $COCH_2NR_{11}R_{12}$, $CONR_{11}COOR_{12}$ or $SO_2R_{12}$ in which $R_{11}$ and $R_{12}$ are as above defined, or $R_9$ and $R_{10}$ together with the nitrogen atom to which they are attached form:
  (f) a morpholino ring optionally substituted with $C_1$–$C_4$ alkyl or $C_1$–$C_4$ alkoxy,
  (g) a piperazino ring optionally substituted by $C_1$–$C_6$ alkyl, $C_2$–$C_6$ alkenyl or phenyl optionally substituted by one or more, for example 1, 2 or 3, substituents selected from $C_1$–$C_6$ alkyl, $C_1$–$C_6$ alkoxy, F, Br, Cl, $CF_3$, OH, $NH_2$ or CN, or
  (h) a pyrrolidino or piperidino, or tetrahydropyridino ring optionally substituted by OH, $NH_2$, COOH, $COOR_{11}$ or $CONR_{11}R_{12}$ wherein $R_{11}$ and $R_{12}$ are as above defined, $C_1$–$C_6$ alkyl, $C_2$–$C_6$ alkenyl or phenyl optionally substituted by one or more, for example 1, 2 or 3, substituents selected from $C_1$–$C_6$ alkyl, $C_1$–$C_6$ alkoxy, F, Br, Cl, $CF_3$, OH, $NH_2$ or CN;

a group of formula $OR_6$ or $SR_6$ in which $R_6$ is as above defined;

a group of formula O-Ph wherein the phenyl (Ph) ring is optionally substituted by nitro, amino or $NR_9R_{10}$ as above defined;

a group of formula B

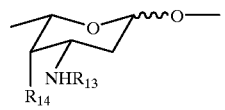

(B)

wherein $R_{13}$ represents hydrogen, $COR_{11}$ wherein $R_{11}$ is as above defined, or a peptidyl residue and $R_{14}$ is halogen or a group of formula $OSO_2R_7$ wherein $R_7$ is as above defined; or a group of formula C or D:

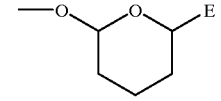

(C)

-continued

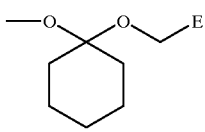
(D)

wherein E is a group of formula COOR$_{11}$ or CONR$_9$R$_{10}$ in which R$_9$, R$_{10}$ and R$_{11}$ are as above defined; and R$_5$ represents hydrogen, hydroxy, a group of formula OR$_6$ or NR$_9$R$_{10}$ wherein R$_6$, R$_9$ and R$_{10}$ are as above defined, or a group of formula F:

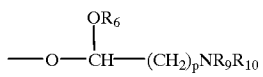
(F)

wherein R$_6$, R$_9$ and R$_{10}$ are as above defined and p is from 1 to 6; and the pharmaceutically acceptable salts thereof.

In a further aspect of the present invention there are provided novel anthracyclinones of the formula A as above defined, with the following provisos:

R$_5$ does not represent NR$_9$R$_{10}$ wherein R$_9$ and R$_{10}$ are as above defined under a) to c) or e) to h) when R$_1$ is H, OH or OCH$_3$ R$_2$ is H, R$_3$ is OH and R$_4$ is a group of formula XCH$_2$OH or XCH$_3$ wherein X is as above defined;

R$_5$ does not represent H or OR when R$_1$ is H, OH or OCH$_3$, R$_2$ is H, OH, COOCH$_3$ and R$_4$ is a group of the formula, XCH$_3$ or XCH$_2$OH, wherein X is as above defined;

R$_4$ does not represents COCH$_2$OR'$_6$ wherein R'$_6$ is phenyl, benzyl, C$_1$–C$_6$ alkyl or C$_5$–C$_6$ cycloalkyl when R$_1$ is H or OH, R$_5$ and R$_4$ are OH and R$_2$ is H;

the compound of formula A is not one of the following derivatives:
14-(N-morpholino)-daunomycinone;
14-(N-piperidino)-daunomycinone;
14-acetamido-daunomycinone;
14-acetamido-4-demethoxy daunomycinone;
14-(N-morpholino)-carminomycinone;
14-(N-methyl-N-piperazino)-daunomycinone;
14-(N-morpholino)carminomycinone;
14-(N-methyl-N-piperazine) carminomycinone.

Each alkyl, alkoxy or alkenyl group may be a straight chain or branched chain group.

A C$_1$–C$_{12}$ alkyl group is preferably a C$_1$–C$_6$ alkyl, more preferably a C$_1$–C$_4$ alkyl group. A C$_1$–C$_6$ alkyl group is preferably a C$_1$–C$_4$ alkyl group. A C$_1$–C$_6$ alkyl group is preferably methyl, ethyl, n-propyl, iso-propyl, n-butyl, t-butyl, sec-butyl or n-pentyl. A C$_1$–C$_4$ alkyl group is preferably methyl, ethyl, n-propyl, iso-propyl, n-butyl, t-butyl or sec-butyl.

A C$_3$–C$_6$ cycloalkyl group is preferably a C$_{5-6}$ cycloalkyl group. A C$_{5-6}$ cycloalkyl group is preferably cyclopentyl or cyclohexyl.

A C$_2$–C$_{12}$ alkenyl group is preferably a C$_2$–C$_6$ alkenyl group, more preferably a C$_2$–C$_4$ alkenyl group. A C$_2$–C$_6$ alkenyl group is preferably a C$_2$–C$_4$ alkenyl group. Preferred alkenyl groups are ethenyl and propenyl.

A peptidyl residue may comprise up to 6, for example 1 to 4, amino acid residues. Suitable peptide residues are selected from Gly, Ala, Phe, Leu, Gly-Phe, Leu-Gly, Val-Ala, Phe-Ala, Leu-Phe, Phe-Leu-Gly, Phe-Phe-Leu, Leu-Leu-Gly, Phe-Tyr-Ala, Phe-Gly-Phe, Phe-Leu-Gly-Phe, Gly-Phe-Leu-Gly, Gly-Phe-Leu-Gly.

In the present, R$_1$ is preferably hydrogen or methoxy. R$_2$ is preferably hydrogen. R$_3$ is preferably hydroxy. R$_4$ is preferably a group of formula XCH$_2$R$_8$ in which X is CO, CH$_2$ or a group of formula:

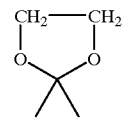

and R$_8$ is hydrogen, a group of formula NR$_9$R$_{10}$, a group of formula O-Ph wherein the Ph ring is optionally substituted by NR$_9$R$_{10}$, a group of formula B or a group of formula C wherein R$_9$ and R$_{10}$ are each independently selected from:

(a') hydrogen, (b') C$_1$–C$_4$ alkyl optionally substituted by O(CH$_2$)$_n$NR$_{11}$R$_{12}$ or NR$_{11}$R$_{12}$ wherein n, R$_{11}$ and R$_{12}$ are as above defined, (d') benzyl optionally substituted on the phenyl ring by one or more, for example 1, 2 or 3, substituents selected from C$_1$–C$_4$ alkyl, C$_1$–C$_4$ alkoxy, F, Br, Cl, CF$_3$, OH, NH$_2$ or CN, or (e') COCF$_3$ or COCH$_2$NR$_{11}$R$_{12}$ wherein R$_{11}$ and R$_{12}$ are as above defined, or R$_9$ and R$_{10}$ together with the nitrogen atom to which they are attached form:

(f') a morpholino ring, (g') a piperazino ring optionally substituted by C$_1$–C$_4$ alkyl, or (h') a pyrrolidino or piperidino ring, or tetrahydropyridino, R$_{13}$ in the group of formula B is hydrogen, R$_{14}$ in the group of formula B is I or OSO$_2$(C$_1$–C$_4$ alkyl) and E in the group of formula C is a group of formula CONR'$_9$R'$_{10}$ wherein R'$_9$ and R'$_{10}$ together with the nitrogen atom to which they are attached form a piperazino ring optionally substituted by C$_1$–C$_4$ alkyl. More preferably R$_4$ is a group of formula

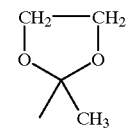

or a group of formula XCH$_2$R$_8$ wherein X is CO or CH$_2$ and R$_8$ is hydrogen, a group of formula NR$_9$R$_{10}$, a group of formula O-Ph wherein the Ph ring is optionally substituted by NH$_2$ or NHCOCH$_2$N(C$_1$–C$_4$ alkyl)$_2$, a group of formula B or a group of formula C wherein R$_9$ and R$_{10}$ are each independently selected from:

(a'') hydrogen, (b'') a methyl or ethyl group optionally substituted by O(CH$_2$)$_n$NH$_2$ or NH$_2$ wherein n is as above defined, (d'') benzyl optionally substituted on the phenyl ring by 1, 2 or 3 substituents selected from C$_1$–C$_4$ alkyl and C$_1$–C$_4$ alkoxy, or (e'') COCF$_3$ or COCH$_2$N(C$_1$–C$_4$ alkyl)$_2$, or R$_9$ and R$_{10}$ together with the nitrogen atom to which they are attached form:

(f") a morpholino ring, (g") a piperazino ring optionally substituted by $C_1$–$C_4$ alkyl, or (h") a pyrrolidino, piperidino or 1,2,3,6 tetrahydropyridino ring, $R_{13}$ in the group of formula B is hydrogen, $R_{14}$ in the group of formula B is I or $OSO_2(C_1$–$C_4$ alkyl) and E in the group of formula C is a group of formula $CONR'_9R'_{10}$ wherein $R'_9$ and $R'_{10}$ together with the nitrogen atom to which they are attached form a piperazino ring optionally substituted by $C_1$–$C_4$ alkyl.

$R_5$ is preferably hydrogen, hydroxy or a group of formula $NR_9R_{10}$ as above defined.

The present invention provides the salts of those compounds of formula A that have salt-forming groups, especially the salts of the compounds having a carboxylic group, a basic group (e.g. an amino group); the salts are especially physiologically tolerable salt, for example alkali metal and alkaline earth metal salts (e.g. sodium, potassium, lithium, calcium and magnesium salts), ammonium salts, salts with an appropriate organic amine or amino acid (e.g. arginine, procaine salts) and the addition salts formed with suitable organic or inorganic acids, for example hydrochloric acid, sulfuric acid, carboxylic acid and sulfonic organic acids (e.g. acetic, trifluoroacetic, p-toluensulphonic acid).

The present invention encompasses all the possible stereoisomers as well as their racemic or optically active mixtures. Preferably $R_3$ is in the α-configuration, i.e. below the plane of the ring.

Specific examples of the preferred compounds for the use of the present invention are those listed hereinunder:

A1: 14-(N-morpholino)-daunomycinone

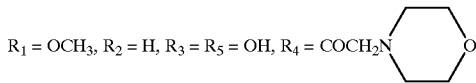

A2: 14-(N-piperidino)-daunomycinone

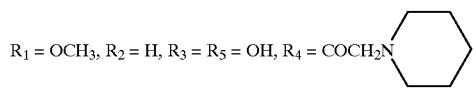

A3: 14-(N-pyrrolidino)-daunomycinone

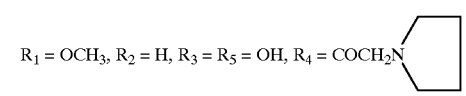

A4: 14-[N-(N'-methyl)-piperazino]-daunomycinone

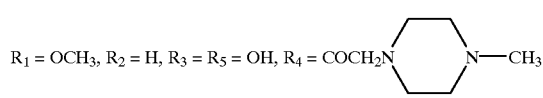

A5: 14-(3',4'-dimethoxybenzylamino)]-daunomycinone $R_1$=$OCH_3$, $R_2$=H, $R_3$=$R_5$=OH, $R_4$=$COCH_2NHCH_2$ [$C_6H_3(OCH_3)_2$]

A6: 14-aminoethyloxyethylamino-daunomycinone $R_1$=$OCH_3$, $R_2$=H, $R_3$=$R_5$=OH, $R_4$=$COCH_2NH$ $(CH_2)_2O(CH_2)_2NH_2$ A7: 14-aminoethylamino-daunomycinone $R_1$=$OCH_3$, $R_2$=H, $R_3$=$R_5$=OH, $R_4$=$COCH_2NH$ $(CH_2)_2NH_2$ A8: 14-(N-aminoethyl-N-trifluoroacetylamino)-daunomycinone $R_1$=$OCH_3$, $R_2$=H, $R_3$=$R_5$=OH, $R_4$=$COCH_2N$ $(COCF_3)(CH_2)_2NH_2$ A9: 14-(N-aminoethyloxyethyl-N-trifluoroacetylamino)-daunomycinone $R_1$=$OCR_3$, $R_2$=H, $R_4$=$COCH_2N$ $(COCF_3)(CH_2)_2O$ $(CH_2)_2NR_2$, $R_3$=$R_5$=OH A10: 4-demethoxy-14-(N-morpholino)-daunomycinone

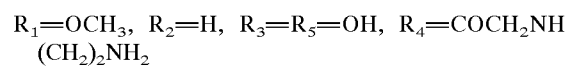

A11: 4-demethoxy-14-(N-pyrrolidino)-daunomycinone

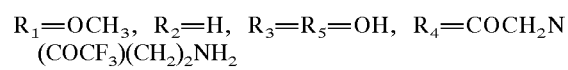

A12: 4-demethoxy-14-(N-pyrrolidino)-daunomycinone

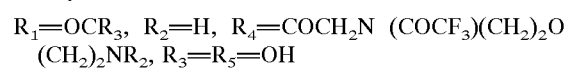

A13: 4-demethoxy-14-N-[(N'-methyl)-piperazino]-daunomycinone

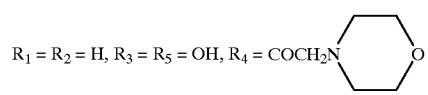

A14: 4-demethoxy-14-(3',4'-dimethoxybenzylamino) daunomycinone $R_1$=$R_2$=H, $R_3$=$R_5$=OH, $R_4$=$COCH_2NHCH_2[C_6H_3$ $(OCR_3)_2]$ A15: 4-demethoxy-14-aminoethyloxyethylamino-daunomycinone $R_1$=$R_2$=H, $R_3$=$R_5$=OH, $R_4$=$COCH_2NH(CH_2)_2O$ $(CH_2)_2NH_2$ A16: 4-demethoxy-14-(N-aminoethyloxyethyl-N-trifluoroacetylamino)-daunomycinone $R_1$=$R_2$=H, $R_3$=$R_5$=OH, $R_4$=$COCH_2N(COCFC_3)$ $(CH_2)_2O(CH_2)_2NH_2$ A17: 7-deoxy-14-(N-morpholino)-daunomycinone

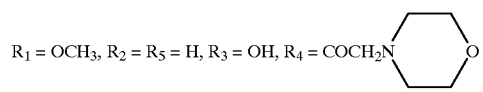

A18: 7-deoxy-14-(N-piperidino)-daunomycinone

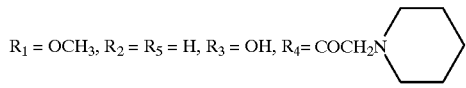

A19: 7-deoxy-14-(N-pyrrolidino)-daunomycinone

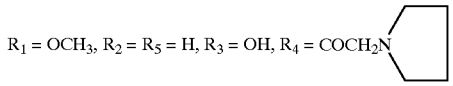

A20: 7-deoxy-14-[N-(N'-methyl)-piperazino]-daunomycinone

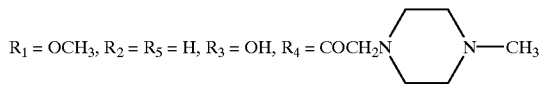

A21: 7-deoxy-14-(3',4'-dimethoxybenzylamino)-daunomycinone
$R_1$=OCH$_3$, $R_2$=$R_5$=H, $R_3$=OH, $R_4$=COCH$_2$NHCH$_2$[C$_6$H$_3$(OCH$_3$)$_2$]

A22: 7-deoxy-14-aminoethyloxyethylamino-daunomycinone
$R_1$=OCH$_3$, $R_2$=$R_5$=H, $R_3$=OH, $R_4$=COCH$_2$NH(CH$_2$)$_2$O(CH$_2$)$_2$NH$_2$ A23: 7-deoxy-14-(N-aminoethyloxyethyl-N-trifluoroacetylamino)-daunomycinone
$R_1$=OCH$_3$, $R_2$=$R_5$=H, $R_3$=OH, $R_4$=COCH$_2$N(COCF$_3$)(CH$_2$)$_2$O(CH$_2$)$_2$NH$_2$ A24: 4-demethoxy-7-deoxy-14-(N-morpholino)-daunomycinone

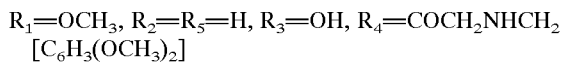

A25: 4-demethoxy-7-deoxy-14-(N-piperidino)-daunomycinone

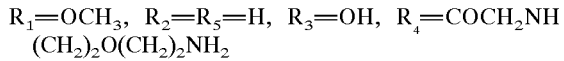

A26: 4-demethoxy-7-deoxy-14-(N-pyrrolidino)-daunomycinone

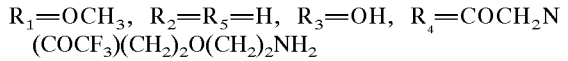

A27: 4-demethoxy-7-deoxy-14-[N-(N'-methyl)-piperazino]-daunomycinone

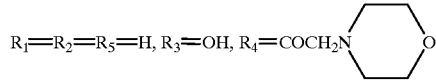

A28: 4-demethoxy-7-deoxy-14-(3',4'-dimethoxybenzylamino)-daunomycinone
$R_1$=$R_2$=$R_5$=H, $R_3$=OH, $R_4$=COCH$_2$NHCH$_2$[C$_6$H$_3$(OCH$_3$)$_2$]

A29: 4-demethoxy-7-deoxy-14-aminoethyloxyethylamino-daunomycinone
$R_1$=$R_2$=$R_5$=H, $R_3$=OH, $R_4$=COCH$_2$NH(CH$_2$)$_2$O(CH$_2$)$_2$NH$_2$ A30: 7-deoxy-7-(N-morpholino)-daunomycinone

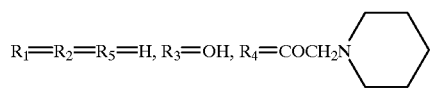

A31: 7-deoxy-7-[bis(2'-hydroxyethyl)]amino-daunomycinone
$R_1$=OCH$_3$, $R_2$=H, $R_3$=OH, $R_4$=COCH$_3$, $R_5$=N(CH$_2$CH$_2$OH)$_2$ A32: 7-deoxy-7-(3',4'-dimethoxybenzylamino)]-13-deoxo-13-ethylene-dioxy-daunomycinone
$R_1$=OCH$_3$, $R_2$=H, $R_3$=OH, $R_4$=C(OCH$_2$CH$_2$O)CH$_3$, $R_5$=NHCH$_2$C$_6$H$_3$(OCH$_3$)$_2$ A33: 7-deoxy-7-benzylamino-13-deoxo-13-ethylenedioxy-daunomycinone
$R_1$=OCH$_3$, $R_2$=H, $R_3$=OH, $R_4$=C(OCH$_2$CH$_2$O)CH$_3$, $R_5$=NHCH$_2$C$_6$H$_5$ A34: 7-deoxy-7-(2'-hydroxyethylamino)-13-deoxo-13-ethylenedioxy-daunomycinone
$R_1$=OCH$_3$, $R_2$=H, $R_3$=OH, $R_4$=C(OCH$_2$CH$_2$O)CH$_3$, $R_5$=NHCH$_2$CH$_2$OH A35: 4-demethoxy-7-deoxy-7-(3',4'-dimethoxybenzylamino)-13-deoxo-13-ethylenedioxy-daunomycinone
$R_1$=$R_2$=H, $R_3$=OH, $R_4$=C(OCH$_2$CH$_2$O)CH$_3$, $R_5$=NHCH$_2$C$_6$H$_3$(OCH$_3$)$_2$ A36: 7-deoxy-7-(3',4'-dimethoxybenzylamino)-daunomycinone $R_1$=OCH$_3$, $R_2$=H, $R_3$OH, $R_4$=COCH$_3$, $R_5$=NHCH$_2$C$_6$H$_3$(OCH$_3$)$_2$ A37: 7-deoxy-7-benzylamino-daunomycinone
$R_1$=OCH$_3$, $R_2$=H, $R_3$=OH, $R_4$=COCH$_3$, $R_5$=NHCH$_2$C$_6$H$_5$ A38: 7-deoxy-7-(2'-hydroxyethylamino)-daunomycinone
$R_1$=OCH$_3$, $R_2$=H, $R_3$=OH, $R_4$=COCH$_3$, $R_5$=NHCH$_2$CH$_2$OH A39: 4-demethoxy-7-deoxy-7-(3',4'-dimethoxybenzylamino)-daunomycinone
$R_1$=$R_2$=H, $R_3$=OH, $R_4$=COCH$_3$, $R_5$=NHCH$_2$C$_6$H$_3$(OCH$_3$)$_2$ A40: 7-deoxy-7-amino-13-deoxo-13-ethylenedioxy-daunomycinone
$R_1$=OCH$_3$, $R_2$=H, $R_3$=OH, $R_4$=C(OCH$_2$CH$_2$O)CH$_3$, $R_5$=NH$_2$ A41: 4-demethoxy-7-deoxy-7-amino-13-deoxo-13-ethylenedioxy-daunomycinone
$R_1$=$R_2$=H, $R_3$=OH, $R_4$=C(OCH$_2$CH$_2$O)CH$_3$, $R_5$=NH$_2$ A42: 7-deoxy-7-aminodaunomycinone
$R_1$=OCH$_3$, $R_2$=H, $R_3$=OH, $R_4$=COCH$_3$, $R_5$=NH$_2$ A43: 4-demethoxy-7-deoxy-7-aminodaunomycinone
$R_1=R_2=H$, $R_3=OH$, $R_4=COCH_3$, $R_5=NH_2$
A44: 13-deoxo-14-(N-morpholino)-daunomycinone

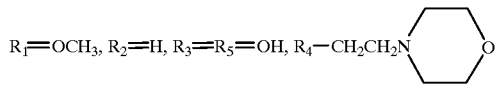

$R_1=OCH_3$, $R_2=H$, $R_3=R_5=OH$, $R_4=CH_2CH_2N$-morpholino

A45: 4-demethoxy-13-deoxo-14-(N-morpholino)-daunomycinone

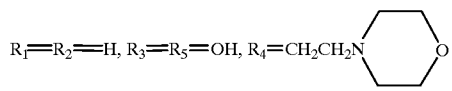

$R_1=R_2=H$, $R_3=R_5=OH$, $R_4=CH_2CH_2N$-morpholino

A46: 13-deoxo-14-aminoethyloxyethylamino-daunomycinone
$R_1=OCH_3$, $R_2=H$, $R_3=R_5=OH$, $R_4=CH_2CH_2NH(CH_2)_2O(CH_2)_2NH_2$
A47: 7-deoxy-14-O-(3'-amino-4'-methansulfonyl-2', 3',4',6'-tetradeoxy-L-lyxohexopyranosyl)-daunomycinone
$R_1=OCH_3$, $R_2=R_5=H$, $R_3=OH$, $R_4=COCH_2R_8$ wherein $R_8$ is a group of formula B wherein $R_{13}=H$ and $R_{14}=OSO_2CH_3$
A48: 7-deoxy-14-O-(3'-amino-4'-iodo-2',3',4',6' tetradeoxy-L-lyxohexopyranosyl)daunomycinone
$R_1=OCH_3$, $R_2=R_5=H$, $R_3=OH$, $R_4=COCH_2R_8$ wherein $R_8$ is a group of formula B wherein $R_{13}=H$ and $R_{14}=I$
A49: 7-deoxy-14-O-[2'-(1"-piperazinyl)-carbonyltetrahydropyran-6'-yl]-daunomycinone

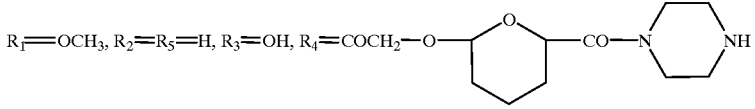

$R_1=OCH_3$, $R_2=R_5=H$, $R_3=OH$, $R_4=COCH_2-O-$...

A50: 14-(p-aminophenyloxy)-daunomycinone
$R_1=OCH_3$, $R_2=H$, $R_3=R_5=OH$, $R_4=COCH_2O-C_6H_4(pNH_2)$
A51: 14-[p-(dimethylaminomethylcarbonylamino)phenyloxy]daunomycinone
$R_1=OCH_3$, $R_2=H$, $R_3=R_5=OH$, $R_4=COCH_2O-C_6H_4[pNHCOCH_2N(CH_3)_2]$
A52: 4-demethoxy-14-(p-aminophenyloxy)-daunomycinone
$R_1=R_2=H$, $R_3R_5=OH$, $R_4=COCH_2O-C_6H_4(p-NH_2)$
A53: 4-demethoxy-14-[p-(dimethylaminomethylcarbonylamino) phenyloxy]-daunomycinone
$R_1=R_2=H$, $R_3=R_5=OH$, $R_4=COCH_2O-C_6H_4[p-NHCOCH_2N(CH_3)_2]$
A54: 7-deoxy-14-(p-aminophenyloxy)-daunomycinone
$R_1=OCH_3$, $R_2=R_5H$, $R_3=OH$, $R_4=COCH_2O-C_6H_4(p-NH_2)$
A55: 7-deoxy-14-[p-(dimethylaminomethylcarbonylamino)phenyloxy]-daunomycinone
$R_1=OCH_3$, $R_2=H$, $R_5=R_3=OH$, $R_4=COCH_2O-C_6H_4[p-NHCOCH_2N(CH_3)_2]$ A56: 7-deoxy-4-demethoxy-14-(p-aminophenyloxy)-daunomycinone
$R_1=R_2=R_5=H$, $R_3=OH$, $R_4=COCH_2O-C_6H_4(p-NH_2)$
A57: 7-deoxy-4-demethoxy-14[p-(dimethylaminomethylcarbonylaminomethyl)phenyloxy]-daunomycinone
$R_1=R_2=R_5=H$, $R_3=OH$, $R_4=COCH_2O-C_6H_4[pNHCOCH_2N(CH_3)_2]$
A58: 14-[N-diethylamino]-daunomycinone
$R_1=OCH_3$, $R_2=H$, $R_3=R_5=OH$, $R_4=COCH_2N(C_2H_5)_2$
A59: 13-dihydro-14-(N-morpholino)-daunomycinone
$R_1=OCH_3$, $R_2=H$, $R_3=R_5=OH$, $R_4=CHOHCH_2N(CH_2)_2O$
A60: 7-deoxy-13-dihydro-14-(N-morpholino)-daunomycinone
$R_1=OCH_3$, $R_2=R_5=H$, $R_3=OH$, $R_4=CHOHCH_2N(CH_2)_2O$
A61: 4-demethoxy-7-deoxy-10-hydroxy-14-(N-morpholino)-daunomycinone
$R_1=R_5=H$, $R_2=OH$, $R_4=COCH_2N(CH_2)_2O$
A62: 4-demethoxy-4-hydroxy-7-deoxy-7-(N-morpholino) daunomycinone
$R_1=OH$, $R_2=H$, $R_3=OH$, $R_4COCH_3$, $R_5=N(CH_2)_2O$
A63: 4-demethoxy-7, 9-dideexy-14-(N-morpholino)-daunomycinone
$R_1=R_3=R_3=R_5=H$, $R_4=COCH_2N(CH_2)_2O$
A64: 4-demethoxy, 4-hydroxy, 14-(N-morpholino) daunomycinone
$R_1=R_3=R_5=OH$, $R_2=H$, $R_4=COCH_2N(CH_2)_2O$ The compounds of formula A may be prepared, depending on the nature of the substituents, starting known anthracyclinones by appropriate chemical modifications. Processes for preparing compounds of formula A and pharmaceutically acceptable salts thereof are as follows:

(i) A preferred process for the preparation of a compound of formula A wherein $R_1$ is $OR_6$ wherein $R_6$ is as above defined, $R_2$ is hydrogen or $COOCH_3$, $R_3$ is OH, $R_4$ is $C_1$ or $C_2$ alkyl or $COCH_3$ and $R_5$ is hydrogen, OH or $OCOOC_2H_5$, or a pharmaceutically acceptable salt thereof, comprises:

(1) protecting the 6-, 11- and, if present, 7-hydroxy groups of a compound of formula G

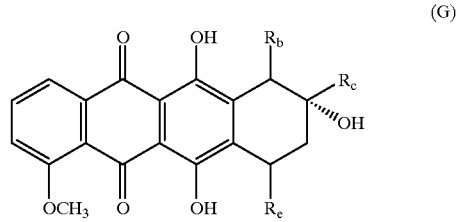

(G)

wherein $R_b$ represents hydrogen or $COOCH_3$, $R_c$ is $C_1$ or $C_2$ alkyl or $COCH_3$ and $R_e$ is hydrogen or hydroxy, as a derivative of formula G1

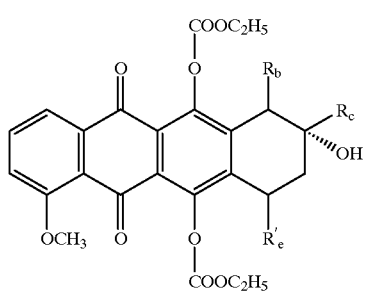

(G1)

wherein $R_b$ and $R_c$ are as previously defined and $R'_e$ is hydrogen or the group $OCOOC_2H_5$;

(2) demethylating such derivative of formula G1 and reacting the resulting 4-hydroxy compound of formula G2

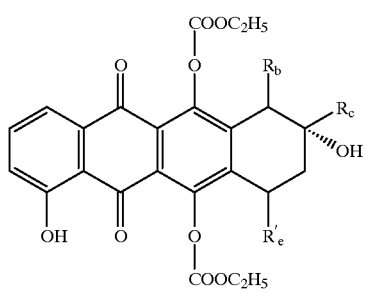

(G2)

wherein $R_b$, $R_c$ and $R'_e$ are as defined above, with the appropriate haloderivative of formula $R_6Hal$, in which $R_6$ is as above defined and Hal is halogen, preferably iodine;

(3) deblocking the 6- and 11-phenolic hydroxy groups of the resulting 4-O-alkyl derivative, thus obtaining a compound of formula G3

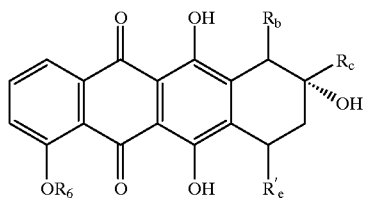

(G3)

wherein $R_6$, $R_b$, $R_c$ and $R'_e$ are as above defined and, if desired when $R'_e$ is $OCOOC_2H_5$, deblocking the 7-hydroxy group of compound G3; and (4) if desired, converting the resulting said compound of formula A into a pharmaceutically acceptable salt thereof.

(ii) In another example, a preferred process for the preparation of a compound of formula A wherein $R_1$ represents a group of formula $OSO_2R_7$ as above defined, $R_2$ is hydroxy or $COOCH_3$, $R_3$ is OH, $R_4$ is $C_1$ or $C_2$ alkyl or $COCH_3$ and $R_5$ is hydrogen or hydroxy, or a pharmaceutically acceptable salt thereof, comprises treating an anthracyclinone of formula H

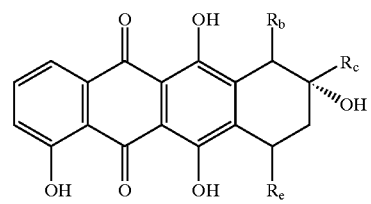

(H)

wherein $R_b$ is hydroxy or $COOCH_3$, $R_c$ is $C_1$ or $C_2$ alkyl or $COCH_3$ and $R_e$ is hydrogen or hydroxy, with the appropriate haloderivative of formula $HalSO_2R_7$ (Hal is halogen, preferably chlorine atom); and, if desired, converting the resulting said compound of formula A into a pharmaceutically acceptable salt thereof.

(iii) In another example, a preferred process for the preparation of compounds of formula A wherein $R_3$ is OH, $R_4$ is $COCH_3$ and $R_5$ is a group of formula $NR_9R_{10}$ wherein $R_9$ and $R_{10}$ are as above defined with proviso that $R_9$ or $R_{10}$ do not represent hydrogen or group of formula $COR_{11}$ or $COOR_{11}$ as above defined, or a pharmaceutically acceptable salt thereof, comprises reacting an aglycone of formula K

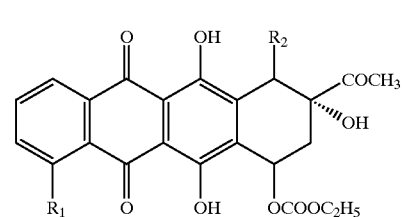

(K)

wherein $R_1$ and $R_2$ are as previously defined, with the appropriate amine derivative of formula $NHR_9R_{10}$, $R_9$ and $R_{10}$ are as above defined; and, if desired, converting the resulting said compound of formula A into a pharmaceutically acceptable salt thereof.

(iv) In another example, a preferred process for the preparation of compounds of formula A wherein $R_3$ is OH, $R_4$ is $COCH_3$ and $R_5$ is a group of formula $NR_9R_{10}$ wherein one of $R_9$ and $R_{10}$ is hydrogen atom and the other does not represent hydrogen or group of formula $COR_{11}$ or $COOR_{11}$ as above defined, or a pharmaceutically acceptable salt thereof, comprises:

(1) protecting an aglycone of formula K as above defined as a 13-ethylenedioxy derivative of formula K1

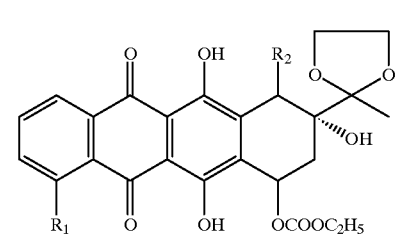

(K1)

wherein $R_1$ and $R_2$ are as above defined;

(2) reacting the said derivative of formula K1 with the appropriate compound of formula $NHR_9R_{10}$, $R_9$ and $R_{10}$ are as above defined;

(3) deblocking the 13-carbonyl group of the resulting 7-amino-substituted derivative of formula K2

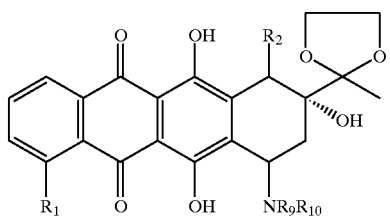

(K2)

wherein $R_1$, $R_2$, $R_9$ and $R_{10}$ are as above defined; and, if desired, converting the said compound of formula A into a pharmaceutically acceptable salt thereof, such as acidifying the compound A to obtain the acid addition salt.

(v) In another example, a preferred process for the preparation of compounds of formula A wherein $R_3$ is OH, $R_4$ is $COCH_3$ and $R_5$ is $NH_2$, or a pharmaceutically acceptable salt thereof, comprises:
(1) treating a derivative of formula K2, as above defined, in which $NR_9R_{10}$ represents 3',4'-dimethoxybenzylamino with an oxidising agent;
(2) deblocking the 13-carbonyl group from the resultant 7-amino-substituted compound of formula K3

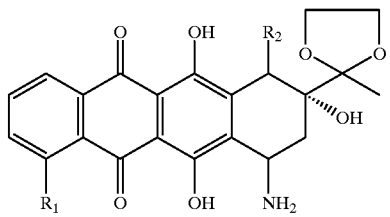

(K3)

wherein $R_1$ and $R_2$ are as above defined; and
(3) if desired, converting the resulting said compound of formula A into a pharmaceutically acceptable salt thereof such as acidifying the compound A to obtain the acid addition salt.

(vi) In another example, a preferred process for the preparation of compounds of formula A wherein $R_3$ is OH or H, $R_4$ is $COCH_2NR_9NR_{10}$ wherein $R_9$ and $R_{10}$ are as above defined with the proviso that they do not represent a group of formula $COR_{11}$ or $COOR_{11}$, and $R_5$ is hydrogen or OH, or a pharmaceutically acceptable salt thereof, comprises:
(1) converting a compound of formula L

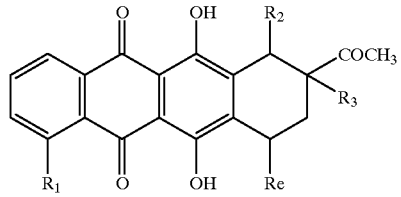

wherein $R_1$, $R_2$, $R_3$ and $R_e$ are as above defined, into the corresponding 14-bromo derivative of formula L1

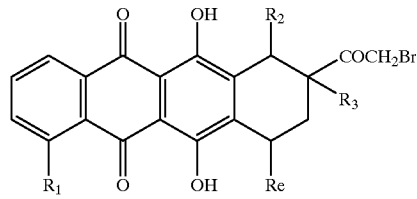

wherein $R_1$, $R_2$, $R_3$ and $R_e$ are as above defined;
(2) reacting the 14-bromo derivative of formula L1 with the appropriate amine of formula $NHR_9R_{10}$ wherein $R_9$ and $R_{10}$ are as previously defined with the proviso that they do not represent a group of formula $COR_{11}$ or $COOR_{11}$; and
(3) if desired, converting the resulting said compound of formula A into a pharmaceutically acceptable salt thereof such as acidifying the compound A to obtain the acid addition salt.

(vii) In another example, a preferred process for the preparation of compounds of formula A wherein $R_4$ is a group of formula $COCH_2O$-Ph wherein the phenyl (Ph) ring is optionally substituted by nitro, amino or $NR_9R_{10}$ as above defined, and $R_5$ is hydrogen or hydroxy, or a pharmaceutically acceptable salt thereof, comprises
(1) reacting a compound of formula L1, as above defined, with a phenol optionally substituted as defined above, preferably nitrophenol, in the form of a salt; and
(2) if desired, converting the resulting said compound of formula A into a pharmaceutically acceptable salt thereof.

(viii) In another example, a preferred process for the preparation of compounds of formula A wherein $R_4$ is a group of formula $XCH_2R_8$ wherein $R_8$ represents a group of formula C and D as above defined, or a pharmaceutically acceptable salt thereof, comprises reacting an anthracyclinone bearing a hydroxylated side chain at the 9-position, such as $COCH_2OH$ or $CH_2CH_2OH$, with a derivative of formula C' or D'

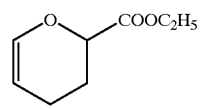

(C')

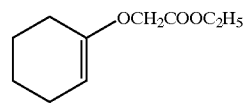

(D')

(2) if desired, hydrolysing the resulting ester derivative, thus obtaining anthracyclinones of formula A bearing a carboxy group on the acetal moiety; and
(3) if desired, converting the resulting said compound of formula A into a pharmaceutically acceptable salt thereof.

(ix) In another example, a preferred process for the preparation of compounds of formula A wherein $R_4$ is a group $CH_2CH_2R_8$, comprises:
(1) transforming a compound of formula A, as above defined, wherein $R_4$ is a group of formula $COCH_2R_8$ into the corresponding 13-hydrazone derivative, preferably a 13-[(4-fluoro)benzenesulfonyl] hydrazone;

(2) reducing the above mentioned hydrazone derivative by using a reducing agent in conditions capable of preserving the nature of the quinone system of the compound of formula A; and (3) if desired, converting the resulting said compound of formula A wherein $R_4$ is a said group $CH_2CH_2R_8$ into a pharmaceutically acceptable salt thereof.

It should be noted that, if desired, derivatives of formula A produced according to processes (i), (ii), (iii), (iv), (v), (vi), (vii), (viii) and (ix) can be further modified at different parts of the molecule by combining processes above described or by means of synthetic procedures described for the anthracyclines or anthracyclinones (see: F. Arcamone in "Doxorubicin", Medicinal Chemistry Vol 17, Academic Press, 1981) or by means of general synthetic procedures (see: J. March, "Advanced organic Reaction" Fourth Ed., J. Wiley & Sons, 1992). For example the compounds of formula A wherein X is a CO group may be converted into a compound of formula A wherein X is CHOH by reduction, for example with sodium borohydride. A compound of formula A wherein $R_5$ is OH may be converted into the corresponding compound having $R_5$=H by treatment with sodium dithionite The compounds of formula A as defined under (i) may be prepared as described in DE-A-2,750,812, for example by reacting a compound of formula G as above defined with an excess of ethoxy-carbonyl chloride, in pyridine, at room temperature from 1 to 2 hours; then treating the protected derivative G1 with aluminium bromide in dry aprotic solvent, preferably methylene chloride, at room temperature for 3 to 6 hours; alkylating the resulting 4-hydroxy derivative of formula G2 preferably with a iodo-derivative of formula $R_6I$, in aprotic solvent such as methylene chloride or chloroform and in presence of a condensing agent, preferably silver oxide, at temperature from 40 to 60° C. for 6 to 24 hours; then deblocking the hydroxy groups from compound of formula G3 by first eliminating the phenol protecting groups by treatment with morpholine in polar protic solvent such as methanol, at room temperature, for from 1 to 3 hours, and then hydrolysing, if present, the 7-O-ethoxycarbonyl group with a very dilute solution of aqueous sodium hydroxide.

The compounds of formula A as defined under (ii) may be prepared as described in U.S. Pat. No. 4,965,351, for example by dissolving a compound of formula H, as above defined, in a dry apolar solvent such as methylene chloride and treating with a compound of formula $HalSO_2R_7$ as above defined (Hal is halogen), preferably chlorine, in presence of an organic base such as N,N-diisopropylethylamine and a catalytic amount of 4-dimethylamino pyridine, at a temperature from 0 to 30° C., preferably at room temperature, from a few minutes to several hours.

The compounds of formula A as defined under (iii) may be prepared by reacting a compound of formula K as above defined with an amino derivative of formula $NHR_9R_{10}$ as above defined in a dry aprotic solvent such as anhydrous methylene chloride, at a temperature from 10 to 30° C. for a few hours to several days; and, if desired, acidifying the resulting product, preferably with anhydrous hydrogen chloride in methanol, to obtain the acid addition salt.

The compounds of formula A as defined under (iv) may be prepared by reacting a compound of formula K as above defined with ethylene glycol in toluene in presence of an acid catalyst, preferably p-toluensulfonic acid, at reflux temperature for 3 to 6 hours; then reacting the protected derivative K1 with a compound of formula $NHR_9R_{10}$ as previously defined in polar solvent such as pyridine or tetrahydrofurane, preferably at room temperature for one to several days; then deblocking the protected carbonyl group by treating derivative of formula K2 with trifluoroacetic acid with few drops of anisole, preferably at room temperature from 30 minutes to two hours; and, if desired, converting the resulting compound into an acid addition salt, preferably with anhydrous hydrogen chloride in methanol.

The compounds of formula A as defined under (v) may be prepared, for example, by reacting a compound of formula K2 as above defined in which $NR_9R_{10}$ represents the residue 3,4-dimethoxybenzylamino with 2,3-dichloro-5,6-dicyano-1,4-benzoquinone (DDQ) in a mixture of water and methylene chloride, at room temperature for one day; then deblocking the resultant derivative of formula K3, as above defined, with trifluoroacetic acid and anisole at room temperature for one hour; and, if desired, converting the resulting compound into an acid addition salt, preferably with anhydrous hydrogen chloride in methanol.

The compounds of formula A as defined under (vi) may be prepared as described in DE-A-2,557,537, for example by reacting a compound of formula L1, prepared from compound L according to DE-A-1,917,874, with the appropriate amine of formula $NHR_9R_{10}$ wherein $R_9$ and $R_{10}$ are as previously defined with proviso that $R_9$ and $R_{10}$ do not represent a group of formula $COR_{11}$ or $COOR_{11}$ as above defined, in a dry polar solvent such as acetone or dimethylformamide, at a temperature of from about 20 to 60° C., for from 4 to 24 hours, and, if desired, converting the resulting compound into an acid addition salt, preferably with anhydrous hydrogen chloride in methanol.

The compounds of formula A as defined under (vii) may be prepared as described in DE-A-1,917,874, for example by reacting a compound of formula L1, as above defined, with a phenol derivative as previously defined, in aprotic organic solvent such as acetone, in presence of base, preferably potassium or sodium carbonate at temperature from 20 to 60° C.

The compounds of formula A as defined under (viii) may be prepared as described in WO 92/10212 and WO 92/02255, for example by reacting an anthracyclinone as above defined with derivatives of formula C' or D' in presence of acid catalyst, for example pyridinium p-toluensulfonate in aprotic solvent such as methylene chloride at temperature from 10 to 30° C., preferably room temperature and from 3 to 24 hours; and, if desired, hydrolysing the ester derivative with dilute aqueous sodium hydroxide.

The compounds of formula A as defined under (ix) may be prepared as described in GB-A-2238540, for example by reducing the 13-[(4-fluoro)benzensulfonyl]hydrazone derivative of an anthracyclinone of formula A as above defined with sodium cyanoborohydride in organic solvent, such as toluene or dimethylformamide, at temperature from 25 to 80° C., for 6 to 24 hours.

Some of the starting materials for the preparation of compounds of formula A are known. Others may be analogously prepared starting from known compounds by means of known procedures.

For example, the following compounds are known and can be represented by the same formula A:

daunomycinone ($R_1$=OCH$_3$, $R_2$=H, $R_3$=$R_5$=OH, $R_4$=COCH$_3$), adriamycinone ($R_1$=OCH$_3$, $R_2$=H, $R_3$=$R_4$=OH, $R_5$COCH$_2$OH), 4-demethoxydaunomycinone ($R_1$=$R_2$=H, $R_3$=$R_5$=OH, $R_4$=COCH$_3$), carminomycinone: ($R_a$=OH, $R_2$=H, $R_3$=$R_5$=OH, $R_4$=COCH$_3$), β-rhedomycinone ($R_1$=$R_2$=$R_3$=$R_5$=OH, $R_4$=CH$_2$CH$_3$), ε-rhodomycinone ($R_1$=$R_3$=$R_5$=OH, $R_2$=COOCH$_3$, $R_4$=CH$_2$CH$_3$), the corresponding 7-deoxy derivatives ($R_5$=H) (see: F. Arcamone in "Doxorubicin" Medicinal Chemistry, vol.17, Academic Press 1981) or the sugar derivatives of formula M

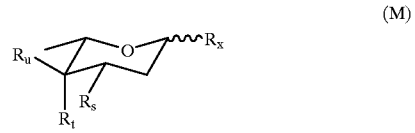

(M)

such as the amino sugars daunosamine, 3-amino- 2,3,6-trideoxy-L-lyxo-hexopyranose, (M1: $R_s$=NH$_2$, $R_t$=$R_x$=OH, $R_u$=H) (see: J.Am.Chem. Soc., 86, 5334, 1964) or acosamine, 3-amino-2,3,6-trideoxy-L-arabino-hexopyranose, (M2: $R_s$=NH$_2$, $R_u$=$R_x$=OH, $R_t$=H) (see: J. Med.Chem., 18, 703, 1975) or the corresponding 1-chloro-3,4-di-trifluoroacetyl daunosaminyl derivatives ($R_x$=Cl and $R_s$=NHCOCF$_3$, $R_t$=OCOCF$_3$) or 1-chloro-3, 4-ditrifluoroacetyl acosaminyl derivatives ($R_x$=Cl and $R_s$=NHCOCF$_3$, $R_u$=OCOCF$_3$).

The compounds of the present invention are characterized by high inhibitory activity on amyloidosis.

The term amyloidosis indicates various diseases whose common characteristic is the tendency of particular proteins to polymerize and precipitate, as insoluble fibrils, into the extracellular space causing structural and functional damage to organ and tissues. The classification of amyloid and amyloidosis has been recently revised in Bulletin of the World Health Organisation 71(1): 105 (1993).

All the different types of amyloid share the same ultrastructural organization in anti-parallel β-pleated sheets despite the fact that they contain a variety of widely differing protein subunits [see: Glenner G. G., New England J.Med. 302 (23): 1283 81980)]. AL amyloidosis is caused by peculiar monoclonal immunoglobulin light chains which form amyloid fibrilis. These monoclonal light chains are produced by monoclonal plasma cells with a low mitotic index which accounts for their well known insensitivity to chemotherapy. The malignancy of these cells consists in their protidosynthetic activity.

The clinical course of the disease depends on the selectivity of organ involvement; the prognosis can be extremely unfavourable in case of heart infiltration (median survival <12 months) or more benign in case of kidney involvement (median survival approx. 5 years).

Considering the relative insensitivity of the amylaidogenic deposits to proteolytic digestion, a molecule that can block or slow amyloid formation and increase the solubility of existing amyloid deposits seems the only reasonable hope for patients with AL amyloidosis. Furthermore, since the supermolecular organization of the amyloid fibrils is the same for all types of amyloid, the availability of a drug that interferes with amyloid formation and increase the solubility of existing deposits, allowing clearance by normal mechanisms, could be of great benefit for all types of amyloidosis, and in particular for the treatment of Alzheimer's disease.

Indeed, the major pathological feature of Alzheimer's Disease (AD), Down syndrome, Dementia pugilistica and Cerebral amyloid angiopaty is amyloid deposition in cerebral parenchyma and vessel walls. These markers are associated with neuronal cell loss in cerebral cortex, limbic regions and subcortical nuclei. Several studies have shown that selective damage to various neuronal systems and synapse loss in the frontal cortex has been correlated with cognitive decline. The pathogenesis and molecular basis of neurodegenerative processes in AD is not known, but the role of β-amyloid, deposited in brain parenahyma and vessel walls has been highlighted by recent report of its neurotoxic activity in vitro and in vivo (Yanker et al. Science, 245: 417, 1990. Kowall et al. PNAS, 88: 7247, 1991). Furthermore, the segregation of familiar AD with mutation of the amyloid precursor protein (APP) gene has aroased interest in the potential pathogenetic function of β-amyloid in AD [Mullan M. et al. TINS, 16(10): 392 (1993)].

The neurotoxicity of β-amyloid has been associated with the fibrillogenic properties of protein. Studies with homologous synthetic peptides indicate that hippocampal cells were insensitive to exposure to fresch β1-42 solution for 24 h while their viability decreased when neurons were exposed to β1-42 previously stored in saline solution for 2–4 days at 37° C. to favour the peptide aggregation. The relationship between fibrils and neurotoxicity is further supported by recent evidence showing that the soluble form of β-amyloid is produced in vivo and in vitro during normal cellular metabolism (Hass et al. Nature, 359, 322, 1993) and only when it aggregate in congophilic formation was associated with distrophic nevrites. On the other hand, non-congophilic "preamyloid" formtion containing single molecule of β-amyloid was not associated with neuronal alteration (Tagliavini et al. Neurosci.Lett. 93: 191, 1988).

The neurotoxicity of β-amyloid has also been confirmed using a peptide homologue β-amyloid fragment 25–35 (β25–35) reteining the self-aggregating properties of the complete β-amyloid fragment β142.

Chronic but not acute exposure of hippocampal neurons to micromolar concentration of β25–35 induced neuronal death by the activation of a mechanism of programmed cell death-known as apoptosis (Forloni et al. NeuroReport, 4: 523, 1993). Here again, neurotoxicity was associated with the self aggregating property of β25–35.

Other neurodegenerative disorder such as spongiform encephalopathy (SE) are characterized by neuronal death and extracellular deposition of amyloid, in this case originated from Prion (PrP) protein. In analogy with the observation that β-amyloid is neurotoxic, the effects of synthetic peptides homologous to different segments of PrP on the viability of primary rat hippocampal neurons have been investigated. The chronic application of peptide corresponding to PrP 106–126 induced neuronal death by apoptosis while under the same conditions all the other peptides tested and the scrambled sequence of PrP 106–126 did not reduce cell viability (Forloni et al., Nature 362: 543). PrP 106–126 resulted highly fibrilogenic in vitro and when stained with Congo red, the peptide aggregate showed green biifrangence indicative of the β-sheets conformation characteristic of amyloid.

The compounds of the present invention can be used to make medicaments useful to prevent or arrest the progression of diseases caused by amyloid proteins, such as AL amyioidosis, Alzheimer's Disease or Down Syndrome and the like.

The present invention also includes, within its scope, pharmaceutical compositions comprising one or more compounds A as active ingredients, in association with pharmaceutically acceptable carriers, excipients or other additives, if necessary.

The pharmaceutical compositions containing a compound of formula A or salts thereof may be prepared in a conventional way by employing conventional non-toxic pharmaceutical carriers or diluents in a variety of dosage forms and ways of administration.

In particular, the compounds of the formula A can be administered:

A) orally, for example, as tablets, troches, lozenges, aqueous or oily suspension, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example maize starch, gelatin or acacia, and lubrificating agents, for example magnesium stearate or stearic acid or talc. The tablets may be uncoated or they may be coated by known techniques to delay disintegration and absorpion in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phophate or kaolin, or a soft gelatin capsules wherein the active ingredient is mixed with water or an oil medium, for example, peanut oil, liquid paraffin or olive oil. Aqueous suspensions contain the active materials in admixture with excipients suitable for the manufacture of aqueous suspensions.

Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and a hexitol anhydrides, for example polyoxyethylene sorbitan monooleate. The said aqueous suspensions may also contain one or more preservatives, for example, ethyl or n-propyl p-hydroxybenzoate, one or more coloring agents, one or more flavouring agents, or one or more sweetening agents, such as sucrose or saccharin. Oily suspension may be formulated by suspending the active ingredient in a vegetable oil, for example arachis oil, olive oil, seseme oil or coconut oil or in a mineral oil such as liquid paraffin. The oily suspensions may contain a thickening agent, for example beewax, hard paraffin or cetyl alcohol. Sweetening agents, such as those set forth above, and flavoring agents may be added to provide a palatable oral preparation. These compositions may be preserved by the addition of an autoxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and agents, may also be present.

The pharmaceutical compositions of the invention may also be in the form of oil-in-water emulsions. The oily phase may be a vegetable oil, for example olive oil or arachis oils, or a mineral oil for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example glycerol, sorbitol or sucrose. Such formulations may also contain a demulcent, a preservative and flavoring and coloring agents.

B) Parenterally, either subcutaneously or intravenously or intramuscularly, or intrasternally, or by infusion techniques, in the form of sterile injectable aqueous or olagenous suspension. The pharmaceutical compositions may be in the form of a sterile injectable aqueous or olagenous suspensions.

These suspensions may be formulated according to the known art using those suitable dispersing of wetting agents and suspending agents which have been above. The sterile injectable preparation may also be a sterile injectable solution or suspension in a non-toxic parenterally-acceptable diluent or solvent for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oils may be conventionally employed including synthetic mono- or diglycerides. In addition fatty acids such as oleic acid find use in the preparation of injectables;

Still a further object of the present invention is to provide a method of controlling amyloidosis diseases by administering a therapeutically effective amount of one or more of the active compounds encompassed by the formula A in humans in need of such treatment.

Daily dose are in range of about 0.1 to about 50 mg per kg of body weight, according to the activity of the specific compound, the age, weight and conditions of the subject to be treated, the type and the severity of the disease, and the frequency and route of administration; preferably, daily dosage levels are in the range of 5 mg to 2 g. The amount of active ingredient that may be combined with the carrier materials to produce a single dosage form will vary depending upon the host treated and the particular mode of administration. For example, a formulation intended for the oral may contain from 5 mg to 2 g of active agent compounded with an appropriate and convenient amount of carrier material which may vary from about 5 to about 95 percent of the total composition. Dosage unit forms will generally contain between from about 5 mg to about 500 mg of the active ingredient.

The following Examples illustrate the invention without limiting it.

EXAMPLE 1

Preparation of 14-(N-morpholino)-daunomycinone (A1)

14-Bromodaunomycinone (L1': $R_1$=OCH$_3$, $R_2$=H, $R_5$=OH) (0.95 g, 2 mmol), prepared as described in J.Org.Chem., 42, 3653 (1977), was dissolved in dry methylene chloride (50 ml), treated with morpholine (0.34 g, 4 mmole) and kept at room temperature for 24 hours. After that, the solvent was removed under reduced pressure and the crude product was flash chromatographed on silicagel using a mixture of methylene chloride and acetone (90:10 by volume) as eluent to give the title compound A1 that was converted into the corresponding hydrochloride (0.8g, yield 77%) by addition of the stoichiometric amount of methanolic hydrogen chloride followed by precipitation with ethyl ether.

TLC on Kieselgel $F_{254}$ (Merck), eluting system methylene chloride/acetone (9:1 by volume), $R_1$=0.5 FD-MS: m/e 483 [M]+ $^1$HNMR (200 MHz, DMSO-d$_6$) δ: 2.03 (dd, J=4.5, 14.2 Hz, 1H, H-8ax); 2.32 (d, J=14.2 Hz, 1H, H-8eq); 2.95 (d, J=18.5Hz, 1H, H-10ax); 3.17 (d, J=18.5 Hz, 1H, H-10eq); 3.2,3.5 (m, 4H, —CH$_2$—N—CH$_2$—); 3.7,4.0 (m, 4H, —CH$_2$—O—CH$_2$—); 4.02 (s, 3H, OCH$_3$); 4.87 (m, 2H, CH$_2$-14); 5.16 (m, 1H, H-7); 5.70 (broad signal, 1H, OH-7); 6.36 (s, 1H, OH-9); 7.68 (m, 1H, H-3); 7.93 (m, 2H, H-1+H-2); 10.40 (broad signal, 1H, NH$^+$); 13.29 (s, 1H, OH-11); 14.01 (s, 1H, OH-6).

EXAMPLE 2

Preparation of 7-deoxy-7-(N-morpholino)-daunomycinone (A30)

7-Ethoxycarbonyl-daunomycinone (K': $R_1$=OCH$_3$, $R_2$=H) (0.94 g, 2 mmol) prepared as described in DE-A-2,750,812 was dissolved in a mixture of methylene chloride (50 ml) and methanol (5 ml), added with morpholine (3 ml) and the mixture was kept at room temperature for 20 hours. After that, the solvent was removed under reduced pressure and the crude material was flash chromatographed on silica gel using a mixture of methylene chloride and acetone (95:5 by volume) as eluting system to give the title compound A30 that was converted into the corresponding hydrochloride (0.5 g, yield 53%) by addition of the stoichiometric amount of methanolic hydrogen chloride followed by precipitation with ethyl ether.

TLC on Kieselgel $F_{254}$ (Merck), eluting system methylene chloridel acetone (9:1 by volume), $R_f$=0.58 FD-MS: m/e 467 [M]+ $^1$HNMR (200 MHz, CDCl$_3$) δ: 1.77 (dd, J=3.3, 14.5 Hz, 1H, H-8ax); 2.32 (dd, J=2.0, 14.5 Hz, 1H, H-8eq); 2.40 (s, 3H, COCH$_3$); 2.50,3.00 (m, 4H, —CH$_2$—N—CH$_2$—); 3.10,3.20 (Abq, J=18.7 Hz, 2H, CH$_2$-10); 3.64 (m, 4H, —CH$_2$—O—CH$_2$—); 4.08 (s, 3H, OCH$_3$); 4.35 (dd, J=2.0, 3.3 Hz, 1H, H-7); 7.38 (d, J=8.3 Hz, 1H, H-3); 7.78 (dd, J=7.7, 8.3 Hz, 1H, H-2); 8.02 (d, J=7.7 Hz, 1H, H-1); 13.29 (s, 1H, OH-11); 14.11 (s, 1H, OH-6).

EXAMPLE 3

Preparation of 7-deoxy-7-(3',4'-dimethoxy-benzylamino)-13-deoxo-13-ethylenedioxy-daunomycinone (A32)

7-Ethoxycarbonyl-daunomycinone (K': 1.88 g, 4 mmol), prepared as above described, was disolved in toluene (100 ml), added with ethylene glycol (3 ml) and pyridinium p-toluen-sulfonate (0.1 g). The mixture was refluxed for 6 hours using a Dean-Stark apparatus to remove the water. After that, the reacion mixture was cooled at room temperature, washed with aqueous 1% sodium hydrogen carbonate, and water. The organic phase was dried over anhydrous sodium sulphate and the organic solvent removed under reduced pressure to give 13-ethylendioxo derivative K' (0.92 g).

TLC on Kieselgel $F_{254}$ (Merck), eluting system methylene chloride/acetone (9:1 by volume), $R_f$=0.25 FD-MS: m/e 518 [M]+

The 13-ethylendioxo derivative K' (0.85 g, 1.64 mmol) was dissolved in a mixture of pyridine (20 ml) and dry tetrahydrofurane (20 ml), added with 3,4-dimethoxy benzylamine (1 ml) and kept at room temperature for two days. After that, the reaction mixture was diluted with methylene chloride (100 ml) and washed with 1N aqueous hydrogen chloride, water and 1% aqueous sodium hydrogen carbonate. The organic phase was separated and the solvent was removed under reduced pressure. The crude material was flash chromatographed on silica gel using a mixture of methylene chloride and acetone (95:5 by volume) as eluting system to give the title compound A32 that was converted into the corresponding hydrochloride by addition of the stoichiometric amount of methanolic hydrogen chloride followed by precipitation with ethyl ether.

TLC on Kieselgel $F_{254}$ (Merck), eluting system methylene chloride/acetone (9:1 by volume), $R_f$=0.8 FD-MS: m/e 607 [M]+ $^1$HNMR (200 MHz, CDCl$_3$) δ: 1.49 (s, 3H, CH$_3$); 1.62 (dd, J=4.0, 14.2Hz, 1H, H-8ax); 2.45 (ddd, J=1.8, 1.8, 14.2 Hz, 1H, H-8eq); 2.86 (d, J=19.1 Hz, 1H, H-10ax); 3.21 (dd, J=1.8, 19.1 Hz, 1H, H-10eq); 3.85, 3.88 (2xs, 6H, OCH$_3$); 4.06 (s, 7H, 4-OCH$_3$+—O—CH$_2$—CH$_2$—O—); 4.44 (dd,J=1.8, 4.0 Hz, 1H, H-7); 6.8–6.9 (m, 3H, H-2'+H-5'+H-6'); 7.34 (dd, J=1.0, 8.5 Hz, 1H, H-3); 7.75 (dd, J=7.8, 8.5 Hz, 1H, H-2); 8.01 (dd, J=10, 7.8 Hz, 1H, H-1)

EXAMPLE 4

Preparation of 7-deoxy-7-(3',4'-dimethoxy-benzylamino) daunomycinone (A36)

Compound A32 (0.3 g) prepared as described in Example 3, was dissolved in trifluoroacetic acid (3 ml) and added with one drop of anisole. After one hour the reaction mixture was diluted with methylene chloride, washed with 1% aqueous sodium hydrogen carbonate, dried over anhydrous sodium sulphate. The organic solvent was removed under reduced pressure and the crude material was flash chromatographed on silicagel, using a mixture of methylene chloride and methanol (95:5 by volume) as eluting system, to give 7-deoxy-7-(3',4'-dimethoxybenzylamino)-daunomycinone (A36) that was converted into the corresponding hydrochloride by addition of the stoichiometric amount of methanolic hydrogen chloride followed by precipitation with ethyl ether.

TLC on Kieselgel $F_{254}$ (Merck), eluting system methylene chloride/methanol (8:2 by volume), $R_f$=0.5 FD-MS: m/e 547 [M]+ $^1$HNMR (200 MHz, DMSO-d$_6$) δ: 2.02 (dd, J=5.0, 14.4 Hz, 1H, H-8ax); 2.34 (s, 3H, COCH$_3$); 2.48 (m, 1H, H-8eq); 2.98,3.08 (Abq, J=19.0 Hz, 2H, CH$_2$-10); 3.74, 3.78 (2xs, 6H, OCH$_3$); 4.00 (s, 3H, 4-OCH$_3$); 4.35 (m, 2H, NH-CH$_2$-aryl); 4.59 (m, 1H, H-7); 6.80 (broad signal, 1H, OH-9); 6.99 (d, J=8.1 Hz, 1H, H-5'); 7.15 (d, J=8.1 Hz, 1H, H-6'); 7.31 (s, 1H, H-2'); 7.69 (m, 1H, H-3); 7.92 (m, 2H, H-1+H-2); 8.5,8.9 (broad signal, 2H, NH$_2^+$); 12.99 (broad signal, 1H, OH-11); 13.94 (broad signal, 1H, OH-6).

EXAMPLE 5

Preparation of 7-deoxy-7-benzylamino-13-deoxo-13-ethylenedioxy-daunomycinone (A33)

13-Ethylendioxo derivative K1' (0.85 g, 1.64 mmol), prepared as described in Example 3, was dissolved in a mixture of methylene chloride (40 ml) and methanol (4 ml), treated with benzylamine (0.5 ml) and kept at room temperature for 18 hours. After that, the solvent was removed under reduced pressure and the crude material was flash chromatographed on silicagel using a mixture of methylene chloride and acetone (9:1 by volume) as eluting system, to give the title compound A33 (0.55 g) that was converted into the corresponding hydrochloride by addition of the stoichiometric amount of methanolic hydrogen chloride followed by precipitation with ethyl ether.

TLC on Kieselgel $F_{254}$ (Merck), eluting system methylene chloride/acetone (9:1 by volume), $R_f$=0.20

EXAMPLE 6

Preparation of 7-deoxy-7-benzylamino-daunomycinone (A37)

Compound A33, prepared as described in Example 5, was treated with trifluoroacetic as described in Example 4, to give 7-deoxy-7-benzylamino-daunomycinone (A37) that was converted into the corresponding hydrochloride by addition of the stoichiometric amount of methanolic hydrogen chloride followed by precipitation with ethyl ether.

TLC on Kieselgel $F_{254}$ (Merck), eluting system methylene chloride/acetone (9:1 by volume), $R_f$=0.60 FD-MS: m/e 487 [M]+ $^1$HNMR (200 MHz, CDCl$_3$) δ: 1.76 (dd, J=4.1, 14.4 Hz, 1H, H-8ax); 2.33 (ddd, J=1.7, 1.9, 14.4 Hz, 1H, H-8eq); 2.42 (s, 3H, COCH$_3$); 2.88 (d, J=18.8 Hz, 1H, H-10ax); 3.14 (dd, J=1.9, 18.8 Hz, 1H, H-10eq); 3.91,4.08 (Abq, J=12.4 Hz, 2H, NH—CH$_2$-aryl); 4.04 (s, 3H, 4-OCH$_3$); 4.41 (dd, J=1.7, 4.1 Hz, 1H, H-7); 7.3–7.4 (m, 6H, C$_6$H$_5$—+H-3); 7.72 (dd, J=7.8, 8.5 Hz, 1H, H-2); 7.94 (dd, J=1.1, 7.8 Hz, 1H, H-1); 13.20 (broad signal, 1H, OH-11) 13.40 (broad signal, 1H, OH-6).

EXAMPLE 7

Preparation of 7-deoxy-7-(2'-hydroxy-ethylamino)-13-deoxo-13-ethylenedioxy-daunolmycinone (A34)

The title compound A34 was prepared according to the procedure described in Example 3, but using ethanolamine.

TLC on Kieselgel $F_{254}$ (Merck), eluting system methylene chloride/methanol (9:1 by volume), $R_f$=0.2 $^1$HNMR (200 MHz, CDCl$_3$) δ: 1.45 (s, 3H, CH$_3$); 1.57 (dd, J=4.1, 14.1 Hz, 1H, H-8ax); 2.37 (ddd, J=1.4, 1.4, 14.1 Hz, 1H, H-8eq); 2.80 (d, J=19.0 Hz, 1H, H-10ax); 3.03 (m, 2H, NH—CH$_2$—OH); 3.11 (dd, J=1.4, 19.0 Hz, 1H, H-10eq); 3.6–4.0 (m, 2H, NH—CH$_2$—OH); 3.99 (s, 3H, OCH$_3$); 4.04 (s, 4H, —O—CH$_2$—CH$_2$—O—); 4.34 (m, 1H, H-7); 7.29 (d, J=7.7 Hz, 1H, H-3); 7.69 (dd, J=7.7, 7.7 Hz, 1H, H-2); 7.88 (d, J=7.7 Hz, 1H, H-1).

EXAMPLE 8

Preparation of 7-deoxy-7-(2'-hydroxyethylamino)-daunomycinone (A38)

The title compound A38 was prepared from compound A34 following the procedure described in Example 4.

TLC on Kieselgel $F_{254}$ (Merck), eluting system methylene chloride/methanol (9:1 by volume), $R_f$=0.5 FD-MS: m/e 441 [M]+$^1$HNMR (200 MHz, CDCl$_3$) δ: 1.80 (dd, J=4.2, 14.4 Hz, 1H, H-8ax); 2.28 (ddd, J=1.8, 2.0, 14.4 Hz, 1H, H-8eq); 2.41 (s, 3H, COCH$_3$); 2.96 (d, J=18.5 Hz, 1H, H-10ax); 3.03 (m, 2H, NH—CH$_2$—CH$_2$—OH); 3.20 (dd, J=1.8, 18.5 Hz, 1H, H-10eq); 3.5–4.0 (m, 2H, NH—CH$_2$—CH$_2$—OH); 4.08 (s, 3H, OCH$_3$); 4.45 (dd, J=2.0, 4.2 Hz, 1H, H-7); 7.39 (J=1.0, 8.5 Hz, 1H,H-3); 7.78 (J=7.7, 8.5 Hz, 1H, H-2); 8.03 (dd, J=1.0, 7.7 Hz, 1H, H-1).

EXAMPLE 9

Preparation of 7-deoxy-13-ethylenedioxy-7-amino-daunomycinone (A40)

7-deoxy-7-(3',4'-dimethoxybenzylamino)-13-deoxo-13-ethylenedioxy-daunomycinone (A32, 0.5 g), prepared as described in Example 3, was dissolved in a mixture of methylene chloride (80 ml) and water (4 ml), added with 2,3-dichloro-5,6-dicyano-1,4-benzo-quinone (DDQ) and kept at room temperature for 24 hours. Then the reaction mixture was washed with 1% aqueous sodium hydrogen carbonate. The organic phase was separated and the solvent removed under reduced pressure to give the title compound A40 (0.3 g).

TLC on Kieselgel $F_{254}$ (Merck), eluting system methylene chloride/methanol (6:1 by volume), $R_f$=0.25

EXAMPLE 10

Preparation of 7-deoxy-7-aminodaunomycinone (A42)

Compound A40 (0.2 g) prepared as described in Example 9, was treated with trifluoroacetic as described in Example 4, to give, after flash chromatography on silicagel using a mixture of methylene chloride and methanol (95:5 by volume), 7-deoxy-7-aminodaunomycinone (A42, 0.14 g) that was converted in the corresponding chloridrate by addition of the stechiometric amount of methanolic hydrogen chloride followed by precipitation with ethyl ether.

TLC on Kieselgel $F_{254}$(Merck), eluting system methylene chloride/methanol (6:1 by volume), $R_f$=0.33 FD-MS: m/e 397 [M]+$^1$HNMR (200 MHz, DMSO-d$_6$) δ: 1.79 (dd, J=5.3, 14.9 Hz, 1H, H-8ax); 2.02 (d, J=14.9 Hz, 1H,H-8eq); 2.29 (s, 3H, COCH$_3$); 2.76 (d, J=18.6 Hz, 1H, H-10ax); 2.89 (d, J=18.6 Hz, 1H, H-10eq); 3.96 (s, 3H, 4-OCH$_3$) 4.31 (d, J=5.3 Hz, 1H, H-7); 7.60 (m, 1H, H-1 +H-2); 8.0 (broad signal, 2H, NH$_2$).

EXAMPLE 11

Preparation of 14-(N-piperidino)-daunomycinone (A2)

14-bromodaunomycinone (L1': $R_f$=OCH$_3$, $R_2$=H, $R_5$=OH) (0.95 g, 2 mmol), prepared as described in J. org. Chem., 42, 3653 (1977) was dissolved in dry methylene chloride (50 ml), trated with piperidine (0.34 g, 4 mmol) and kept at room temperature for 16 hours. The solvent was then removed under reduced pressure and the crude product was flash chromatographed on silica gel eluting with a mixture of methylene chloride and methanol (96:4 by volume) to give the title compound that was converted into the corresponding hydrochloride (0.55 g, yield 53%) by addition of the stoichiometric amount of methanolic hydrogen chloride followed by precipitation with ethyl ether.

TLC on Kieselgel $F_{254}$ (Merck), eluting system methylene chloride/methanol (9:1 by volume), $R_f$=0.5. FAB-MS: m/e 482 [M+H]$^+$ $^1$H-NMR (200 MHz, DMSO-d6) δ:

1.2–1.9 (m, 6H, piperidine $CH_2$-3+$CH_2$-4+$CH_2$-5); 1.97 (dd, J=4.6, 14.1 Hz, 1H, H-8ax); 2.30 (d. J=14.1 Hz, 1H, H-8eq); 2.89 (d, J=18.4 Hz, 1H, H-10ax); 3.0, 3.4 (m, 4H, piperidine $CH_2$-1+$CH_2$-6); 3.13 (d, J=18.4 Hz, 1H, H-10eq); 3.97 (s, 3H, $OCH_3$-4); 4.76 (m, 2H, $CH_2$-14); 5.10 (m, 1H, H-7); 5.60 (d, J=6.6 Hz, 1H, OH-7); 6.39 (s, 1H, OH-9); 7.64 (m, 1H, H-3); 7.90 (m, 2H, H-1+H-2); 9.7 (broad signal, 1H, $HN^+$); 13.23 (s, 1H, OH-11); 13.95 (s, 1H, OH-6)

EXAMPLE 12

Preparation of 14-[N-(N'-methyl)-piperazino]-daunomycinone (A4)

The title compound was prepared analogously as described in examples 1 and 2.

TLC on Kieselgel $F_{254}$ (Merck), eluting system methylene chloride/methyl alcohol (8:2 by volume), $R_f$=0.36. FAB-MS: m/e=497 $[M+H]^+$ $^1$H-NMR (200 MHz, $CDCl_3$) δ: 2.14 (dd, J=4.8, 14.5 Hz, 1H, H-8ax); 2.32 (s, 3H, $NCH_3$); 2.36 (ddd, J=2.0, 2.0, 14.5 Hz, 1H, H-8eq); 2.4–2.7 (m, 8H, piperazine hydrogens); 2.98 (d, J=18.5 Hz, 1H, H-10ax); 3.17 (dd, J=2.0, 18.5 Hz, 1H, H-10eq); 3.60, 3.72 (two doublets, J=16.7 Hz, 2H, $CH_2$-14); 4.0 (broad signal, 1H, OH-7); 4.09 (s, 3H, $OCH_3$-4); 5.27 (dd, J=2.0, 4.8 Hz, 1H, H-7); 6.1 (broad signal, 1H, OH-9); 7.39 (dd, J=1.1, 8.6 Hz, 1H, H-3); 7.78 (dd, J=7.7, 8.6 Hz, 1H, H-2); 8.02 (dd, J=1.1, 7.7 Hz, 1H, H-1); 13.31 (broad signal, 1H, OH-11); 13.97 (s, 1H, OH-6)

EXAMPLE 13

Preparation of 14-[N-diethylamino]-daunomycinone (A58)

The title compound was prepared analogously as described in examples 1 and 2.

TLC on Kieselgel $F_{254}$ (Merck), eluting system methylene chloride/methyl alcohol (9:1 by volume), $R_f$=0.45. FAB-MS: m/e=470 $[M+H]^+$ $^1$H-NMR (200 MHz, $CDCl_3$) δ: 1.15 (t, J=7.2 Hz, 6H, $N(CH_2CH_3)_2$); 2.14 (dd, J=4.8, 14.5 Hz, 1H, H-8ax); 2.37 (ddd, J=2.0, 2.0, 14.5 Hz, 1H, H-8eq); 2.69 (m, 4H, $N(CH_2CH_3)_2$); 2.97 (d, J=18.5 Hz, 1H, H-10ax); 3.21 (dd, J=2.0, 18.5 Hz, 1H, H-10eq); 3.58, 3.73 (two doublets, J=15.4 Hz, 2H, $CH_2$-14); 4.08 (s, 3H, $OCH_3$-4); 5.23 (dd, J=2.0, 4.8 Hz, 1H, H-7); 7.38 (dd, J=1.0, 8.3 Hz, 1H, H-3); 7.76 (dd, J=7.7, 8.3 Hz, 1H, H-2); 8.02 (dd, J=1.0, 7.7 Hz, 1H, H-1); 13.3 (broad signal, 1H, OH-11); 14.0 (broad signal, 1H, OH-6)

EXAMPLE 14

Preparation of 4-demethoxy-14-(N-morpholino)-daunomycinone (A10)

The title compound was prepared as reported in example 1 starting from 4-demethoxy-14-bromodaunomycinone, which was obtained by bromination of 4-demethoxy-daunomycinone according to the procedure described in J. Org. Chem., 42, 3653 (1977) for daunomycinone.

TLC on Kieselgel $F_{254}$ (Merck), eluting system methylene chloride/methyl alcohol (96:4 by volume), $R_f$=0.21. FAB-MS: m/e 454 $[M+H]^+$ $^1$H-NMR (200 MHz, DMSO-d6) δ: 1.96 (dd, J=4.6, 14.3 Hz, 1H, H-8ax); 2. 16 (dd, J=2.0, 14.3 Hz, 1H, H-8eq); 2.44 (m, 4H, $N(CH_2CH_2)_2O$); 2.92, 3.00 (two doublets, J=18.7 Hz, 2H, $CH_2$-10); 3.57 (m, 4H, $N(CH_2CH_2)_2O$); 3.67, 3.72 (two doublets, J=18.9 Hz, 2H, $CH_2$-14); 5.03 (m, 1H, H-7); 5.4 (broad signal, 1H, OH-7); 6.05 (s, 1H, OH-9); 7.96 (m, 2H, H-2+H-3); 8.26 (m, 2H, H-1+H-4); 13.3 (broad signal, 2H, OH-6+OH-11)

EXAMPLE 15

Preparation of 4-demethoxy-7-deoxy-14-(N-morpholino)-daunomycinone (A24)

The title compound was prepared as reported in example 1 starting from 4-demethoxy-7-deoxy-14-bromodaunomycinone, which was obtained by bromination of 4-demethoxy-7-deoxy-daunomycinone according to the procedure described in J. Org. Chem., 42, 3653 (1977) for daunomycinone.

TLC on Kieselgel $F_{254}$ (Merck), eluting system methylene chloride/methyl alcohol (96:4 by volume), $R_f$=0.33. FAB-MS: m/e 438 $[M+H]^+$ $^1$H-NMR (200 MHz, $CDCl_3$) δ: 1.9–2.0 (m, 2H $CH_2$-8); 2.63 (m, 4H, $N(CH_2CH_2)_2O$); 2.8–3.2 (m, 4H, $CH_2$-7+$CH_2$-10); 3.46, 3.60 (two doublets, J=15.0 Hz, 2H, $CH_2$-14); 3.78 (m, 4H, $N(CH_2CH_2)_2O$); 7.82 (m, 2H, H-2+H-3); 8.32 (m, 2H, H-1+H-4); 13.44, 13.46 (two singlets, OH-6+OH-11)

EXAMPLE 16

Preparation of 7-deoxy-14-(N-morpholino)-daunomycinone (A17)

A mixture of 14-(N-morpholino)-daunomycinone (A1) (1.5 g, 3.3 mmol) and 5% palladium on activated carbon (300 mg) in 250 ml of dioxan was shaken under a hydrogen pressure of 2 atm for one hour. The catalyst was then filtered, the solvent evaporated under reduced pressure, and the residue purified by column chromatography on silica gel (eluent methylene chloride/methyl alcohol 96:4 by volume). The title compound was isolated (0.4 g 28%) as a red powder that was converted into the corresponding hydrochloride by addition of the stoichiometric amount of methanolic hydrogen chloride followed by precipitation with ethyl ether.

TLC on Kieselgel $F_{245}$ (Merck), eluting system methylene chloride/methyl alcohol (96:4 by volume), $R_f$=0.20. FAB-MS: m/e 468 $[M+H]^+$ $^1$H-NMR (200 MHz, DMSO-d6) δ: 1.7–2.2 (m, 2H $CH_2$-8); 2.83 (m, 2H $CH_2$-7); 2.91 (m, 2H $CH_2$-10); 3.3, 3.8 (m, 8H, morpholine hydrogens); 3.97 (s, 3H, $OCH_3$-4); 4.8 (m, 2H $CH_2$-14); 6.14 (broad signal, OH-9); 7.65 (m, 1H, H-3); 7.91 (m, 2H, H-1+H-2); 10.4 (broad signal, 1H, $HN^+$); 13.34 (s, 1H, OH-11); 13.85 (s, 1H, OH-6)

EXAMPLE17

Preparation of 13-dihydro-14-(N-morpholino)-daunomycinone (A59)

Magnesium bromide ethyl etherate (2.24 g, 8.68 mmoles) was added dropwise to a stirred suspension of 14-(N-morpholino)-daunomycinone (A1) (2.10 g, 4.34 mmol) in tetrahydrofuran (80 ml ) under argon atmosphere. To the resulting mixture, cooled at −40° C., sodium borohydride (0.164 g, 4.34 mmol) was added portionwise. After stirring at −40° C. for 1.5 hours the reaction was quenched by dropwise addition of methyl alcohol (25 ml). Volatilies were evaporated under reduced pressure and the residue was purified by column chromatography on silica gel (eluent chloroform/methyl alcohol 94:6 by volume). The title compound was isolated (139 g 66%) as a red powder that was converted into the corresponding hydrochloride by addition of the stoichiometric amount of methanolic hydrogen chloride followed by precipitation with ethyl ether.

TLC on Kieselgel $F_{254}$ (Merck), eluting system chloroform/methyl alcohol (94:6 by volume), $R_f$=0.30. FAB-MS: m/e 486 $[M+H]^+$ $^1$H-NMR (200 MHz, DMSO-d6)

δ: 1.7–2.2 (m, 2H CH$_2$-8); 2.3–2.8 (m, 6H, CH$_2$-14+N(CH$_2$CH$_2$) 2O); 2.86 (m, 2H CH$_2$-10); 3.57 (m, 5H, N(CH$_2$CH$_2$)$_2$O+CH-13); 3.97 (s, 3H, OCH$_3$-4); 4.81 (d, J=5.5 Hz, 1H, OH-13); 5.03 (m, 1H, H-7); 5.20 (m, 1H, OH-7); 5.6, 5.8 (broad signal, 1H, OH-9); 7.5–8.0 (m, 3H, H-1+H-2+H-3); 13.3 (broad signal, 1H, OH-11); 13.9 (broad signal, 1H, OH-6)

EXAMPLE 18

Preparation of 7-deoxy-13-dihydro-14-(N-morpholino)-daunomycinone (A60)

A solution of sodium dithionite (2.15 g, 1.23 mmol) in water (8ml) was added dropwise to a stirred solution of 13-dihydro-14-(N-morpholino)-daunomycinone (0.240 g, 0.494 mmol), prepared as described in the previous example, in dimethylformamide (16 ml) at room temperature under argon atmosphere. After stirring 1 hour at room temperature, the reaction mixture was poured into water (250 ml) and extracted with ethyl acetate (6×25 ml). The layers were separated, the organic layer was washed with water, dried over sodium sulphate and evaporated to give 300 mg of raw material, which was purified by column chromatography on silica gel (eluent chloroform/methyl alcohol 96:4 by volume). The title compound was isolated (116 mg, 50%) as a red powder that was converted into the corresponding hydrochloride by addition of the stoichiometric amount of methanolic hydrogen chloride followed by precipitation with ethyl ether.

TLC on Kieselgel F$_{254}$ (Merck), eluting system chloroform/methyl alcohol (96:4 by volume), R$_f$=0.20. FAB-MS: m/e 470 [M+H]$^+$ $^1$H-NMR (400 MHz, DMSO-d6) δ: 1.56 (m, 1H, H-8ax); 1.82 (m, 1H, H-8eq); 2.38 (dd, J=7.7, 12.8 Hz, 1H, CH(H)-14); 2.63 (dd, J=3.7, 12.8 Hz, 1H, CH(H)-14); 2.45 (m, 4H, N(CH$_2$CH$_2$)$_2$O); 2.6–2.9 (m, 4H, CH$_2$-10+CH$_2$-7); 3.53 (m, 4H, N(CH$_2$CH$_2$)$_2$O); 3.53 (m, 1H, CH-13); 3.94 (s, 3H, OCH$_3$-4); 4.65 (d, J=5.1, Hz, 1H, OH-13); 4.76 (broad signal, 1H, OH-9); 7.58 (m, 1H, H-3); 7.86 (m, 2H, H-1+H-2); 13.36 (s, 1H, OH-11); 13.88 (s, 1H, OH-6);

EXAMPLE 19

Preparation of 4-demethoxy-7-deoxy-10-hydroxy-14-(N-morpholino)-daunomycinone (A61)

A solution of ruthenium trichloride hydrate (27 mg, 0.1 mmol) and sodium-periodate (0.48 g, 2.2 mmol) in water (3 ml) was added dropwise to a stirred suspension of 4-demethoxy-7-deoxy-9,10-anhydro-daunomycinone, prepared as described in J. Org: Chem., 48, 2820 (1983), (0.5 g, 1.5 mmol) in ethyl acetate/acetonitrile 1:1 (20 ml) at 0° C. under argon atmosphere. After stirring 0.5 hour at 0° C., the reaction mixture was poured into an aqueous solution of sodium thiosulphate (20 ml) and extracted with methylene chloride. The layers were separated, the organic layer was washed with water, dried over sodium sulphate and evaporated to give 300 mg of raw material, which was purified by column chromatography over silica gel (eluent chloroform/methyl alcohol 50:0.2 by volume). 4-Demethoxy-7-deoxy-10-hydroxy-daunomycinone 241–242° C. (dec.).

4-Demethoxy-7-deoxy-10-hydroxy-14-bromodaunomycinone was prepared from 4-demethoxy-7-deoxy-10-hydroxy-daunomycinone following the bromination procedure described in J.Org.Chem. 42, 3653, (1977) for daunomycinone. Red powder; m.p. 223–225° C. (dec.)

According to the procedure outlined in example 1, 4-demethoxy-7-deoxy-10-hydrxy-14-bromodaunomycinone was converted to the title compound, which was isolated as a red powder powder that was converted into the corresponding hydrochloride by addition of the stoichiometric amount of methanolic hydrogen chloride followed by precipitation with ethyl ether.

TLC on Kiesenlgel F$_{245}$ (Merck), eluting system chloroform/methyl alcohol (96:4 by volume), R$_f$=0.30. FAB-MS: m/e 453 [M+H]$^+$ $^1$H-NMR (200 MHz, DMSO-d6) δ: 1.8–3.0 (m, 4H, CH$_2$-8+CH$_2$-7); 2.36 (m, 4H, N(CH$_2$CH$_2$)$_2$O); 3.47 (m, 4H, N(CH$_2$CH$_2$)$_2$O); 3.59 (s, 2H, CH$_2$-14); 4.90 (s, 1H, H-10); 5.60 (broad signals, 1H, OH-10); 5.67 (s, 1H, H-9); 7.94 (m, 2H, H-2+H-3); 8.27 (m, 2H, H-1+H-4) 13.30 (broad signals, 2H, OH-6+OH-11);

EXAMPLE 20

Preparation of 4-demethoxy-4-hydroxy-7-deoxy-7-(N-morpholino)daunomycinone (A62)

4-demethoxy, 4-hydroxyt O$^6$,O$^7$-diethoxycarbonyldaunomycinone (1.3 g, 2.5 mmol), prepared from 6,7,11 triethoxycarbonyldaunomycinone (G1: R$_b$=H, R$_c$=COCH$_3$, R'$_e$=OCOOC$_2$H$_5$) as described in Il Farmaco, Ed. Sc., 35, 347 (1980), was dissolved in a mixture of methylene chloride (40 ml) and methanol (40 ml) and 1ml of morpholine was added. The mixture was kept at room temperature for 20 hours. The solvent was removed under reduced pressure and the crude material was flash chromatographed on silica gel using a mixture of methylene chloride and acetone (9:1 by volume) as eluting system to give the title compound that was converted into the corresponding hydrochloride (0.3 g, yield 25%) by addition of the stoichiometric amount of methanolic hydrogen chloride followed by precipitation with ethyl ether.

TLC on Kieselgel F$_{254}$ (Merck), eluting system methylene chloride/methanol (9:1 by volume), R$_f$=0.8 FAB-MS: m/e 502 [M+H]$^+$ $^1$H-NMR (200 MHz, DMSO-d6) δ: 1.85 (m, 1H, H-8ax); 2.10 (m, 1H, OCH$_2$CH(Hax)N); 2.20 (m, 1H, H-8eq); 2.32 (d, J=10.7 Hz, 1H, CH(H)-14); 2.40 (m, 2H, NCH$_2$CH$_2$OH); 2.68 (m, 1H, OCH$_2$CH(Heq)N); 2.77, 2.86 (d, J=19.2 Hz, 1H, H-10ax); 2.83 (d, J=10.7 Hz, 1H, CH(H)-14); 3.07, 3.10 (d, J=19.2 Hz, 1H, H-10eq); 3.47 (m, 2H, NCH$_2$CH$_2$OH); 3.57 (m, 1H, NCH$_2$CH(Hax)O); 3.90 (m, 1H, NCH$_2$CH(Heq)O); 3.97 (s, 3H, OCH$_3$-4); 4.40 (m, 1H, CH$_2$OH); 5.00 (m, 1H, H-7); 5.23 (d, J=7.7 Hz, 1H, OH-7); 5.32, 5.34, 5.84, 5.93 (s, 2H, OH-9+OH-13); 7.63 (m, 1H, H-3); 7.87 (m, 2H, H-1+H-2); 13.31 (broad signal, 1H, OH-11); 13.97 (broad signal, 1H, OH-6)

EXAMPLE 21

Preparation of 4-demethoxy-7,9-dideoxy-14-(N-morpholino)-daunomycinone (A63)

4-Demethoxy-7,9-dideoxy-14-bromodaunomycinone was prepared from 4-demethoxy-7,9-dideoxy-10-hydroxy-daunomycinone, prepared as described in Synt. Commun., 15, 1081 (1985), following the bromination procedure described in J.Org.Chem. 42, 3653, (1977) for daunomycinone. According to the procedure outlined in example 1, 4-demethoxy-7,9-dideoxy-14-bromodaunomycinone was converted to the title compound, which was isolated as a red powder that was converted into the corresponding hydrochloride by addition of the stoichiometric amount of methanolic hydrogen chloride followed by precipitation with ethyl ether.

TLC on Kieselgel F$_{254}$ (Merck), eluting system chloroform/methyl alcohol (98:2 by volume), R$_f$=0.23.

FAB-MS: m/e 422 [M+H]$^+$ $^1$H-NMR (200 MHz, pyridine-d5) δ: 1.78 (m, 1H, H-8ax); 2.18 (m, 1H, H-8eq); 2.54 (m, 4H, N(CH$_2$CH$_2$)$_2$O); 2.70 (m, 1H, H-9); 2.9–3.3 (m, 4H, CH$_2$-10+CH$_2$-7); 3.43 (m, 2H CH$_2$-14); 3.78 (m, 4H, N(CH$_2$CH$_2$)$_2$O); 7.75 (m, 2H, H-2+H-3); 8.39 (m, 2H, H-1+H-4); 13.80 (broad signal, 2H, OH-6+OH-11)

EXAMPLE 22

Preparation of 4-demethoxy, 4-hydroxy, 14-(N-morpholino)daunomoycinone (A64)

A suspension of 4-demethoxy, 4-hydroxydaunomycinone (1.4 g, 3.6 mmol), prepared as described in J. Antibiotics, 31, 178 (1978), in 20 ml of dioxane was treated with 10.3 ml of a bromine solution obtained by diluting 1 ml of bromine up to 50 ml with dioxane. The reaction mixture was stirred at room temperature during three hours and the resulting 4-demethoxy, 4-hydroxy, 14-bromodaunomycinone was precipitated by addition of 50 ml of petroleum ether. The precipitate was filtered, washed with petroleum ether and dried under vacuum to give 1.35 g (80% yield) of crude product that was used as such for the next reaction. A suspension of 0.75 g (1.6 mmol) of 4-demethoxy, 4-hydroxy, 14-bromo-daunomycinone in 50 ml of methylene chloride was treated with 0.28 g (3.2 mmol) of morpholine and the resulting mixture was stirred at room temperature during 24 hours. The solvent was then removed under reduced pressure and the crude product was flash chromatographed on silica gel eluting with a mixture of methylene chloride and methanol (95:5 by volume) to give the title compound that was converted into the corresponding hydrochloride (0.16 g, yield 20%) by addition of the stoichiometric amount of methanolic hydrogen chloride followed by precipitation with ethyl ether.

TLC on Kieselgel F$_{254}$ (Merck), eluting system methylene chloride/methanol (9:1 by volume), R$_f$=0.6. FAB-MS: m/e 470 [M+H]$^+$ $^1$H-NMR (400 MHz, DMSO-d6) δ: 2.01 (dd, J=4.7, 14.1 Hz, 1H, H-8ax); 2.31 (dd, J=14.1 Hz, 1H, H-8eq); 2.92, 3.16 (two doublets, J=18.8 Hz, 2H, CH$_2$-10); 3.1–3-3 (m, 4H, N(CH$_2$CH$_2$)$_2$O); 3.7–4.0 (m, 4H, N(CH$_2$CH$_2$)$_2$O); 4.80, 4.87 (two doublets, J=18.8 Hz, 2H, CH$_2$-14); 5.11 (m, 1H, H-7); 5.70 (broad signals, 1H, OH-7); 6.34 (s, 1H, OH-9); 7.41 (m, 1H, H-3); 7.8–7.9 (m, 2H, H-1+H-2); 10.40 (broad signal, 1H, HN$^+$); 11.98 (s, 1H, OH-4); 12.80 (s, 1H, OH-6); 13.40 (s, 1H, OH-11);

Bioloqical Test

Anthracyclinone derivatives of formula A interfere with the self-aggregating activity of β-amyloid fragment 25–35 and PrP fragment 106–126 by using light scattering analysis.

β25–35 (GSNKGAIIGLH) and PrP 106–126 (KTNMKHMAGAAAAGAVVGGLG) were synthesized using solid phase chemistry by a 430A Applied Biosystems Instruments and purified by reverse-phase HPLC (Beckman Inst. mod 243) according to Forloni et al., Nature 362: 543, 1993. Light scattering of the peptide solutions was evaluated by spectrofluorimetriy (Perkin Elmer LS 50B), excitation and emission were monitored at 600 nm. β-amyloid fragment 25–35 and PrP 106–126 were dissolved at a concentration of 0.5 to 1 mg/ml (0.4–0.8 mM and 0.2–0.4 mM respectively) in a solution of phosphate buffer pH 5, 10 mM spontaneously aggregate within an hour.

The tested compounds, dissolved at several concentration (0.2–2 mM) in Tris buffer 5 mM pH 7.4, were added to the peptidic solutions at the moment of their preparation in order to evaluate the process of fibrilogenesis. The compounds prepared in examples 1–22, added at equimolar concentration with β-amyloid fragment 25–35 and PrP 106–126, showed complete prevention of the agregation.

Neurotoxicity.

Neuronal cells were obtained from the cerebral cortex of foetal rats at embryonic day 17 and cultured in the presence of foetal calf serum (10%) as described by Forloni et al., (Mol.Brain.Res. 16: 128, 1992).

The intrinsic cytotoxicity of compounds A has been evaluated by the repeated exposure of the cortical neurons to different concentration of the compounds ranging from the nanomolar to the micromolar concentrations.

Neuronal cell death has been quantifyied by a calorimetric method described by Mossmann et al., (J.Immunol.Meth., 65, 55–63, 1983).

Up to concentration of 10 μM all the tested compounds were devoided of any neurotoxic effect.

What is claimed is:

1. An anthracyclinone of formula A:

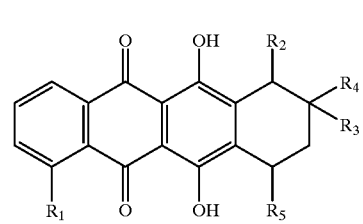

(A)

wherein R$_1$ represents:

hydrogen or hydroxy; or a group of formula OR$_6$ in which R$_6$ is C$_1$–C$_6$ alkyl, C$_{5-6}$ cycloalkyl or CH$_2$Ph with the phenyl (Ph) ring optionally substituted by 1, 2 or 3 substituents selected from F, Cl, Br, C$_1$–C$_6$-alkyl, C$_1$–C$_6$ alkoxy and CF$_3$;

R$_2$ represents hydrogen, hydroxy, OR$_6$, COOH or COOR$_6$ wherein R$_6$ is as above defined;

R$_3$ represents hydrogen, hydroxy, or OR$_6$ as above defined;

R$_4$ represents a group of formula XCH$_2$R$_8$ in which X is CO

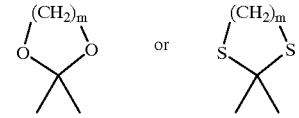

in which R$_8$ is:

a group of formula NR$_9$R$_{10}$ in which:
R$_9$ and R$_{10}$ together with the nitrogen atom to which they are attached form:
(f) A morpholino ring optionally substituted with C$_1$–C$_4$ alkyl or C$_1$–C$_4$ alkoxy,
(g) a piperazino ring optionally substituted by C$_1$–C$_6$ alyl, C$_2$–C$_6$ alkenyl or phenyl optionally substituted by one or more substituents selected from C$_1$–C$_6$ alkyl, C$_1$–C$_6$ alkoxy, F, Br, Cl, CF$_3$, OH, NH$_2$ or CN, or
(h) a pyrrolidino, piperidino or tetrayhdropyridino ring optionally substituted by OH, NH$_2$, COOH, COOR$_{11}$ or CONR$_{11}$R$_{12}$ wherein R$_{11}$ and R$_{12}$ are as above defined, C$_1$–C$_6$ alkyl, $C_2$–$C_6$ alkenyl or phenyl optionally substituted by one of more substituents selected from $C_1$–$C_6$ alkyl, $C_1$–$C_6$ alkoxy, F, Br, Cl, $CF_3$, OH, $NH_2$ or CN;

$R_5$ represents hydrogen, hydroxy or a group of formula $OR_6$ or a pharmaceutically acceptable salt thereof.

2. The anthracyclinone according to claim 1 wherein $R_1$ is hydrogen or methoxy.

3. The anthracyclinone according to claim 1 wherein $R_2$ is hydrogen.

4. The anthracyclinone according to claim 1 wherein $R_3$ is hydroxy.

5. The anthracyclinone according to claim 1 wherein $R_5$ is hydrogen or hydroxy.

6. A pharmaceutical composition which comprises, as active ingredient, an anthracyclinone of formula A as defined in claim 1 or a pharmaceutically acceptable salt thereof in an admixture with a pharmaceutically acceptable carrier or diluent.

* * * * *